(12) United States Patent
Kraus et al.

(10) Patent No.: US 11,168,153 B2
(45) Date of Patent: Nov. 9, 2021

(54) CYCLODEXTRIN-BASED TRANSPORTER OF NUCLEOSIDE TRIPHOSPHATE TRANSPORTER ACROSS THE CELL MEMBRANE, ITS PREPARATION AND USE

(71) Applicant: USTAV ORGANICKE CHEMIE A BIOCHEMIE AV CR, V.V.I., Prague (CZ)

(72) Inventors: Tomas Kraus, Prague (CZ); Zbigniew Zawada, Vendryne (CZ)

(73) Assignee: USTAV ORGANICKE CHEMIE A BIOCHEMIE AV CR, V.V.I., Prague (CZ)

( * ) Notice: Subject to any disclaimer, the term of this patent is extended or adjusted under 35 U.S.C. 154(b) by 473 days.

(21) Appl. No.: 16/084,024

(22) PCT Filed: Mar. 15, 2017

(86) PCT No.: PCT/CZ2017/050013
§ 371 (c)(1),
(2) Date: Sep. 11, 2018

(87) PCT Pub. No.: WO2017/157356
PCT Pub. Date: Sep. 21, 2017

(65) Prior Publication Data
US 2020/0291139 A1    Sep. 17, 2020

(30) Foreign Application Priority Data
Mar. 16, 2016 (CZ) ................ CZ2016-152

(51) Int. Cl.
*C08B 37/16* (2006.01)
*A61K 47/40* (2006.01)
*G01N 33/483* (2006.01)

(52) U.S. Cl.
CPC ..... *C08B 37/0012* (2013.01); *G01N 33/4833* (2013.01); *A61K 47/40* (2013.01)

(58) Field of Classification Search
None
See application file for complete search history.

(56) References Cited

FOREIGN PATENT DOCUMENTS

WO    2012145632 A1    10/2012

OTHER PUBLICATIONS

International Search Report and Written Opinion for corresponding PCT application No. PCT/CZ2017/050013, dated May 8, 2017.

*Primary Examiner* — Layla D Berry
(74) *Attorney, Agent, or Firm* — Notaro, Michalos & Zaccaria P.C.

(57) ABSTRACT

Compounds of general formulae 6 and 13 where X is —NH—C(NH$_2$)=N+H$_2$ or —N+H$_3$, Y is a linear oligomer of arginine units terminated with an aminodimethylenamide unit (-Arg)n-NH—(CH$_2$)$_2$—NH$_2$, where n=6-10, or arginine-aminocaproic units (-Arg-Aca)n-NH$_2$, where n=6 to 10, A-=CF$_3$COO— or Cl— and m=1-2. Preparation and use of compounds of general formula 6 and 13 as carriers of nucleoside triphosphates across the cell membranes for the purpose of incorporation of modified nucleoside triphosphates into cellular DNA or RNA. Use of compounds of general formula 6 and 13 as carriers of nucleoside triphosphates across the cell membrane for determining the virostatic activities of modified nucleoside triphosphates. Use of compounds of general formula 6 and 13 as carriers of modified nucleoside triphosphates across the cell membrane for determining cell proliferation and S phase of the cell cycle.

19 Claims, 6 Drawing Sheets

| Compound (solvent) | H-1 | H-2 | H-3 | H-4 | H-5 | H-6a + H-6b |
|---|---|---|---|---|---|---|
| 3 [a] (DMSO+AcOD) T=40 °C | 5.063<br>4.916<br>4.907<br>4.900 (2)<br>4.898<br>4.894 | 3.75<br>3.42 – 3.34 (6) | 3.62 – 3.57 (7) | 3.40 – 3.32 (7) | 3.78 – 3.72 (7) | 3.78 – 3.73 (7)<br>3.62 – 3.57 (7) |
| 2 [b] (CDCl₃) | 5.092<br>5.063<br>5.015<br>5.012<br>5.009<br>5.007<br>4.845 | 4.794<br>4.760<br>4.757<br>4.746<br>4.732<br>4.725<br>3.251 | 5.290<br>5.259<br>5.248<br>5.234<br>5.225<br>5.221<br>5.155 | 3.74 – 3.59 (7) | 4.00 – 3.92 (6)<br>3.83 | 3.65 – 3.51 (14) |
| 4 [c] (D₂O) | 5.295<br>5.182<br>5.177 (2)<br>5.175<br>5.169<br>5.159 | 3.69 – 3.65 (6)<br>3.585 | 4.065<br>3.99 – 3.95 (6) | 3.61 – 3.58 (7) | 4.07 – 4.03 (7) | 3.42 – 3.38 (7)<br>3.30 – 3.26 (7) |
| 5 [d] (D₂O) | 5.233<br>5.115 (3)<br>5.110 (2)<br>5.104 | 3.65 – 3.68 (6)<br>3.56 | 4.05<br>3.98 – 3.93 (6) | 3.57 – 3.51 (7) | 4.08 – 4.03 (7) | 3.65 – 3.54 (14) |
| 10 [e] (CD₃OD) | 5.24<br>5.047<br>5.031 (4)<br>5.024 | 3.565<br>3.54 – 3.51 (5)<br>3.44 | 3.98<br>3.88 – 3.83 (6) | 3.345 – 3.31 | 3.93 – 3.90 (7) | 3.88 – 3.83 (7)<br>3.64 – 3.57 (7) |
| 14 [f] (DMSO+AcOD) T=45 °C | 5.104<br>4.931 (2)<br>4.930<br>4.928<br>4.923<br>4.919<br>4.913 | 3.739<br>3.76 – 3.73 (7) | 3.61 – 3.56 (7)<br>3.38 | 3.40 – 3.32 (6)<br>3.588<br>3.746 | 3.76 – 3.71 (8) | 3.76 – 3.71 (8)<br>3.60 – 3.54 (8) |

[a] O–CH₂–CH=CH₂: 5.88 ddt ($J$ = 17.2, 10.5, 5.9, 5.9, –CH=); 5.30 dq ($J$ = 17.2, 1.7, 1.6, 1.6, =CHaHb) and 5.17 dq ($J$ = 10.5, 1.7, 1.2, 1.2, =CHaHb), 4.31 ddt ($J$ = 12.7, 5.9, 1.6, 1.2, O–CHaHb–); 4.20 ddt ($J$=12.7, 5.9, 1.6, 1.2, O–CHaHb–).
[b] O–CH₂–CH=CH₂: 5.75 dddd ($J$ = 17.3, 10.3, 5.9, 5.5, –CH=); 5.20 dq ($J$ = 17.3, 1.6, 1.5, 1.5, =CHaHb), 5.15 dq ($J$ = 10.3, 1.5, 1.3, 1.2, =CHaHb), 4.00 ddt ($J$ = 13.1, 5.9, 1.5, 1.2, O–CHaHb–) and 3.92 ddt ($J$ = 13.1, 5.5, 1.6, 1.3, O–CHaHb–); 2.041 s, 2.016 s, 2.014 s (4x), 2.007 s, 1.997 s, 1.995 s, 1.991 s, 1.988 s, 1.963 s and 1.934 s (13x OAc).
[c] O–CH₂–CH=CH₂: 5.96 ddt ($J$ = 17.2, 10.3, 6.2, 6.2, –CH=); 5.38 dq ($J$ = 17.2, 1.5, 1.5, 1.5, =CHaHb); 5.31 dq ($J$ = 10.3, 1.5, 1.2, 1.2, =CHaHb), 4.27 dt ($J$ = 6.2, 1.5, 1.2, O–CH₂–).
[d] O–CH₂–CH=CH₂: 5.95 ddt ($J$ = 17.2, 10.4, 6.3, 6.3, –CH=); 5.37 dq ($J$ = 17.2, 1.5, 1.4, 1.4, =CHaHb); 5.30 dq ($J$ = 10.4, 1.5, 1.0, 1.0, =CHaHb), 4.25 dt ($J$ = 6.3, 1.4, 1.0, O–CH₂–).
[e] O–CH₂–CH=CH₂: 5.97 dddd ($J$ = 17.2, 10.3, 6.7, 5.9, –CH=); 5.33 dq ($J$ = 17.2, 1.5, 1.5, 1.5, =CHaHb); 5.22 dq ($J$ = 10.3, 1.7, 1.0, 1.0, =CHaHb), 4.36 ddt ($J$ = 12.4, 5.9, 1.3, 1.3, O–CHaHb–); 4.24 ddt ($J$ = 12.4, 6.7, 1.2, 1.2, O–CHaHb–).
[f] O–CH₂–CH=CH₂: 5.89 dddd ($J$ = 17.3, 10.4, 6.1, 5.7, –CH=); 5.30 dq ($J$ = 17.3, 1.5, 1.5, 1.5, =CHaHb); 5.17 ddt ($J$ = 10.3, 1.8, 1.2, 1.2, =CHaHb), 4.30 ddt ($J$ = 12.7, 5.7, 1.5, 1.4, O–CHaHb–); 4.24 ddt ($J$ = 12.4, 6.7, 1.2, 1.2, O–CHaHb–).

Fig. 11

| Compound (solvent) | C-1 | C-2 | C-3 | C-4 | C-5 | C-6 |
|---|---|---|---|---|---|---|
| 3 [a] (DMSO+AcOD) T=40°C | 102.35<br>102.28 (3)<br>102.26<br>102.14<br>100.58 | 72.37<br>72.20<br>72.19<br>72.16 (2)<br>72.11<br>71.92 | 72.83<br>72.75<br>72.73 (3)<br>72.69<br>72.65 | 83.94<br>83.52<br>83.43<br>83.40<br>83.38<br>83.36<br>79.51 | 70.55 (5)<br>70.26<br>70.19 | 51.54 (6)<br>51.49 |
| 2 [b] (CDCl$_3$) | 97.25<br>95.88<br>95.82<br>95.79<br>95.42<br>95.37<br>95.18 | 76.61<br>69.44 (2)<br>69.37<br>69.31<br>69.28<br>68.88 | 71.08<br>70.11<br>69.54 (2)<br>69.49<br>69.44<br>68.11 | 77.74<br>76.48<br>76.22<br>76.08<br>75.82<br>75.52<br>75.13 | 71.54 (2)<br>71.41<br>71.33 (2)<br>71.28<br>70.91<br>70.58 | 50.62<br>50.56<br>50.47<br>50.43 (2)<br>50.37<br>50.24 |
| 4 [c] (D$_2$O) | 104.18<br>104.13<br>104.12<br>104.11<br>104.09<br>103.99<br>102.66 | 81.28<br>74.44<br>74.38 (2)<br>74.34<br>74.33<br>74.16 | 74.86<br>74.81<br>74.80<br>74.49<br>74.76<br>74.74<br>73.95 | 85.37<br>84.45 (3)<br>84.42<br>84.40<br>84.37 | 70.54<br>70.52<br>70.51<br>70.49 (2)<br>70.28<br>70.25 | 42.56<br>42.50 (4)<br>42.36 (2) |
| 5 [d] (D$_2$O) | 104.62<br>104.55<br>104.53<br>104.50 (2)<br>104.41<br>102.90 | 81.51<br>74.49<br>74.46<br>74.44<br>74.42 (2)<br>74.26 | 75.15 (5)<br>75.14<br>75.11 | 85.90<br>85.37<br>85.23 (3)<br>85.21 (2) | 74.19<br>73.60 (2)<br>73.58 (2)<br>73.45<br>73.37 | 44.92 (7) |
| 10 [e] (CD$_3$OD) | 103.79<br>103.76<br>103.75<br>103.72<br>103.69<br>103.58<br>102.27 | 81.00<br>74.02<br>73.98<br>73.97<br>73.96<br>73.95<br>73.77 | 74.25<br>74.21<br>74.20 (2)<br>74.19<br>74.16<br>73.74 | 86.06<br>85.40<br>85.28<br>85.26<br>85.24<br>85.21<br>85.20 | 71.56 (3)<br>71.54<br>71.51<br>71.32<br>71.25 | 41.68<br>41.61 (2)<br>41.59<br>41.58<br>41.57<br>41.48 |
| 14 [f] (DMSO+AcOD) T=45 °C | 102.28<br>102.26 (2)<br>102.23<br>102.20<br>102.17<br>102.00<br>100.47 | 72.55<br>72.53<br>72.50<br>72.47<br>72.44<br>72.42<br>72.32 | 72.90<br>72.88<br>72.68<br>72.65<br>72.63<br>72.61<br>72.59 | 83.09<br>82.92<br>82.90<br>82.87 (2)<br>82.76<br>82.75 (2) | 70.71 (3)<br>70.65 (2)<br>70.35<br>70.31 | 51.46<br>51.43<br>51.42<br>51.40 (2)<br>51.37 (2)<br>51.35 |

[a] O–CH$_2$–CH=CH$_2$: 134.66 (–CH=), 118.12 (=CH$_2$), 72.89 (O–CH$_2$–).
[b] 13xOAc: 169.78, 169.74, 169.62, 169.58, 169.55, 169.51, 168.65, 168.47, 168.42(2), 168.40(2) and 168.13 (13x CO), 19.98, 19.83, 19.81, 19.79, 19.78, 19.76, 19.74 and 19.72(6) (13xCH$_3$), O–CH$_2$–CH=CH$_2$: 133.11 (–CH=), 116.98 (=CH$_2$), 71.22 (O–CH$_2$–).
[c] O–CH$_2$–CH=CH$_2$: 135.76 (–CH=), 122.53 (=CH$_2$), 75.95 (O–CH$_2$–); TFA: 119.12 q (J(C,F) = 292.0, –CF$_3$), 165.58 q (J(C,F) = 35.2, COOH).
[d] O–CH$_2$–CH=CH$_2$: 135.74 (–CH=), 122.55 (=CH$_2$), 75.88 (O–CH$_2$–); H$_2$N–C(=NH)–NH–: 160.43.
[e] O–CH$_2$–CH=CH$_2$: 135.29 (–CH=), 119.37 (=CH$_2$), 74.72 (O–CH$_2$–); 7xCF$_3$CONH: 117.47 q (J(C,F) = 286.5, –CF$_3$), 159.48 q (J(C,F) = 35.7, COOH).
[f] O–CH$_2$–CH=CH$_2$: 134.78 (–CH=), 118.01 (=CH$_2$), 72.84 (O–CH$_2$–).

CYCLODEXTRIN-BASED TRANSPORTER OF NUCLEOSIDE TRIPHOSPHATE TRANSPORTER ACROSS THE CELL MEMBRANE, ITS PREPARATION AND USE

FIELD OF ART

The invention falls within the industrial and scientific fields. Nucleoside triphosphate transporter across the cell membrane can be used both in the search for new drugs and for further development in experimental cell biology.

BACKGROUND ART

Chemically modified analogues of nucleosides are widely used in the pharmaceutical industry as virostatic and anti-cancer drugs (Jordheim et al., 2013). The mechanisms of their action include mostly inhibiting processes leading to virus replication, or cell replication. In most cases, the applied nucleoside analogues alone are not active; they become active only after enzyme catalysed phosphorylation cascade, leading to the formation of nucleoside triphosphates or phosphonate diphosphates. Only these substances are active metabolites; e.g. virostatic modified nucleotides can inhibit the replication of the virus, most often through inhibition of reverse transcriptase, which catalyses the process of transcription of genetic information from ribonucleic acid (RNA) virus into deoxyribonucleic acid (DNA) of the host cell. Another known mechanism is the incorporation of such a modified nucleotide analogue into DNA, which prevents the continuation of the DNA strand synthesis, and thus stops the replication of cells. Similar mechanisms may also be applied in inhibiting the synthesis of RNA viruses.

At present, unphosphorylated chemically modified analogues of nucleosides are used for testing and administration of the drugs as phosphorylated nucleotides do not pass through the cell membrane. However, modified nucleosides are known to be phosphorylated with a low conversion in the cell, because particularly enzymes catalysing the synthesis of monophosphates (monophosphate kinases) are very specific. This led to the development of so-called "prodrugs" which can be monophosphates or monophosphonates whose phosphate (or phosphonate) function is converted to e.g. an ester; this derivative much more easily penetrates through the cell membrane, its monophosphate (monophosphonate) is regenerated by enzymatically catalysed cleavage in the cytosol and further enters a phosphorylation cascade, whose product is an active triphosphate. However, no universally ideal "prodrug" exists; conversely, finding an optimal structure of phosphate derivative requires testing a number of structural analogues, and in search for active substances, prodrug derivatives preparation is only proceeded if the mother nucleoside exhibits activity.

From the above it is clear that in the search for new active substances, undesirable elimination of potentially very active substances may occur only because i) their transport across the cell membrane fails, or ii) the nucleosides are not phosphorylated in the cell, since it is not technically and economically feasible to prepare all potentially active derivatives—"prodrugs" for each new structure of the nucleoside analogues. It is obvious that the process of discovery of new active substances could be considerably more effective, if active metabolites, i.e. triphosphates of nucleosides were directly tested in the cellular models, or in vivo. However, these substances cannot pass through the cell membrane, so it such a procedure was not possible yet. The literature reported several approaches to solving this problem. Attempts to transport modified nucleoside triphosphates (NTPs hereinafter) in the form of complexes with liposomes or polymers bearing amino groups were described (Hillaireau & Couvreur, 2009); however, these showed very little effectivity. From the published works, the experiments of Vinogradov et al. can be considered a sufficiently confirmed transport of NTPs; they complexed NTPs into nanogels which fuse with cell membranes and NTPs are released into the cytosol in the process. Proof has been performed monitoring fluorescent-labelled NTPs (Vinogradov et al., 2005a) and determining the cytostatic activity of fludarabine-5-triphosphate (Vinogradov et al., 2005b). A principal disadvantage of the carrier (nanogel) is difficult reproducibility of the process, since the polymer material (nanogel) is not accurately defined. Furthermore, the published work (Vinogradov et al., 2005a) shows that fluorescently labeled NTP is localized mainly outside the cell nucleus, i.e., the method of transport is not suitable in cases where incorporation into the genomic DNA is desired, which occurs in the cell nucleus.

Another recently published method of solving the problem of impermeability of NTP across the cell membrane is the preparation of nucleoside triphosphate modified with diesters on γ-phosphate, which is then, after penetration into the cytosol, enzymatically digested (Gollnest et al., 2015). It is therefore a "prodrug" approach with all its specifics and with the need to optimize the structure for each case of application.

DISCLOSURE OF THE INVENTION

The present invention provides compounds (transporters), which are capable of forming defined complexes with an NTP via noncovalent interactions with the NTP receptor (cyclodextrin unit) and to transport them across the cell membrane into the intracellular millieu. There, the modified nucleoside triphosphates are released by competitive displacing with natural NTPs, in particular adenosine triphosphate, which reaches up to millimolar concentrations in the cytosol, i.e. several orders of magnitude higher than the expected desired concentration of the modified NTP in the cytosol (micromolar concentrations). Released NTP quickly, in a matter of minutes, concentrates in the cytosol and the cell nucleus, where it can act as an inhibitor of RNA or DNA polymerases. Assuming that it is a substrate of the relevant enzyme (polymerase), it may optionally be incorporated into RNA or DNA. The novelty of the solution described herein lies in the simplicity and versatility of use for any nucleoside triphosphate without its further chemical modification, since the essence of the interaction between NTP and "binding site" in the transporter is a noncovalent interaction of any triphosphate group with the cyclodextrin unit modified with amino groups, or guanidine groups. An advantage of our method of NTP transport is the possibility to prepare a complex of the transporter with NTP derived from any nucleoside, and to transport it quickly to the cell cytosol and nucleus. It is not necessary to prepare a series of prodrug derivatives for each NTP, whose enzymatically catalysed cleavage to a free NTP in the cell depends on structural parameters that cannot be reliably predicted.

The complex of NTP with the carrier is prepared by dissolving the NTP and the carrier in a medium, whose composition is given below, and it is directly applied to the cell culture for a period of minutes to several tens of minutes.

The invention subject includes a compound of general formula 6 where X stands for —NH—C(NH$_2$)=N$^+$H$_2$ CF$_3$COO$^-$ or —N$^+$H$_3$ CF$_3$COO$^-$ and Y is a linear (6)

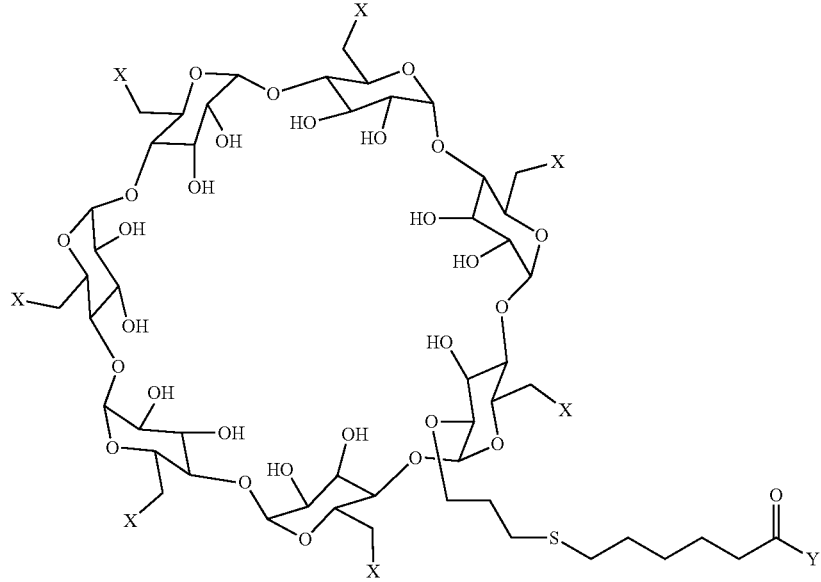

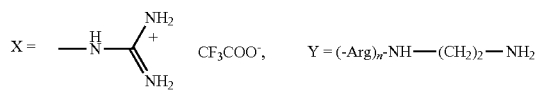

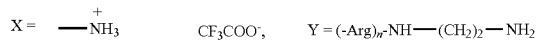

oligomer consisting of arginine units terminated with an aminodimethylenamide unit (-Arg)$_n$-NH—(CH$_2$)$_2$—NH$_2$, where n=6-10, or arginine-aminocaproic units (-Arg-Aca)$_n$-NH$_2$, where n=6 to 10.

The invention subject also includes a method of the preparation of compounds, whose starting material is heptakis(6-azido-6-deoxy)-β-cyclodextrin of formula 1

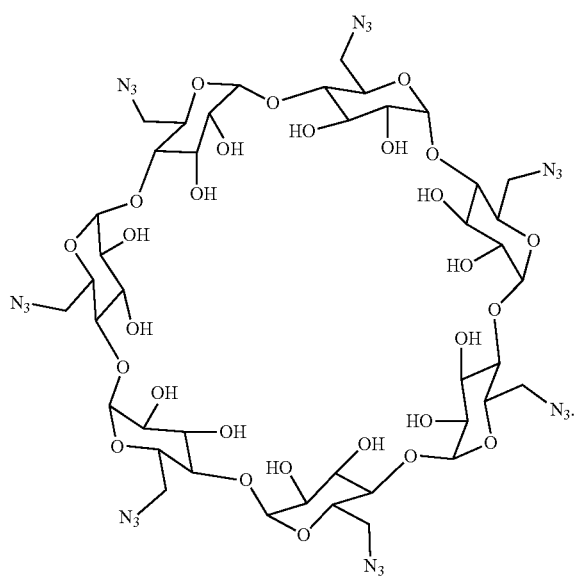

(1)

This compound, treated with allyl bromide and sodium hydride in dimethylformamide, followed by separation, is converted to a mixture of $2^I$-O-allyl-heptakis(6-azido-6-deoxy)-β-cyclodextrin and $3^I$-O-allyl-heptakis(6-azido-6-deoxy)-β-cyclodextrin. The mixture, treated with acetic anhydride, N,N-diisopropylethylamin and N,N-dimethylaminopyridin is acetylated and after chromatographic separation, compound of structure 2 is isolated

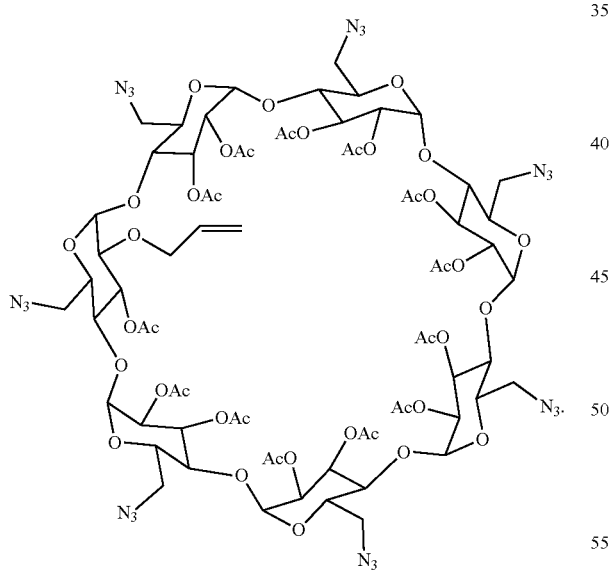

(2)

In the next step, compound 2 is deacetylated by treatment with sodium methanolate in anhydrous methanol. The product is $2^I$-O-allyl-heptakis(6-azido-6-deoxy)-β-cyclodextrin of structural formula 3.

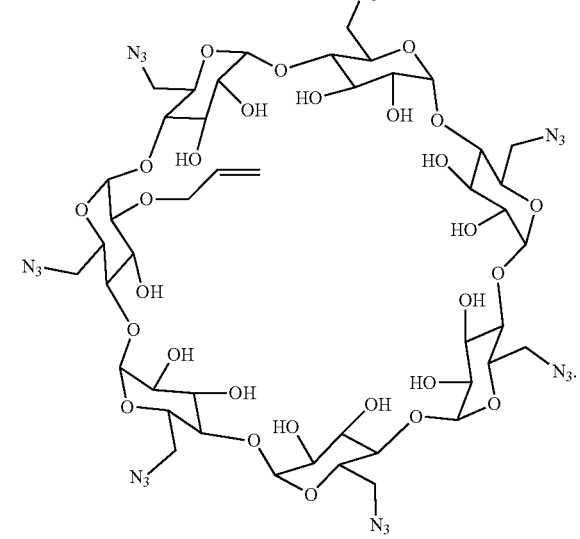

(3)

Compound 3 is treated with triphenyl phosphine and aqueous ammonia in a DMF solvent and converted to $2^I$-O-allyl-heptakis(6-amino-6-deoxy)-β-cyclodextrin heptakis(trifluoroacetate) of structural formula 4

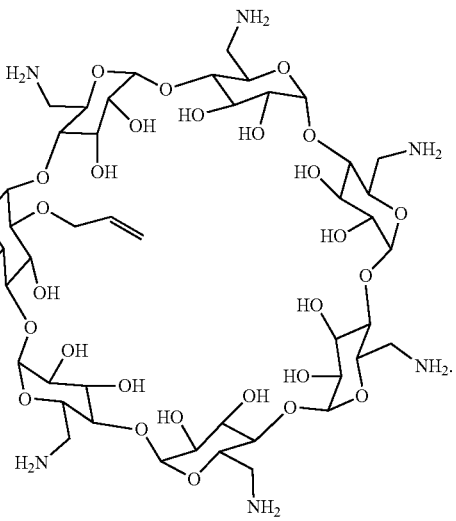

(4)

Derivative 4 is treated with 1H-pyrazole-1-carboxamidine hydrochloride and converted to $2^I$-O-allyl-heptakis(6-guanidino-6-deoxy)-β-cyclodextrin heptakis (trifluoroacetate) of structural formula 5.

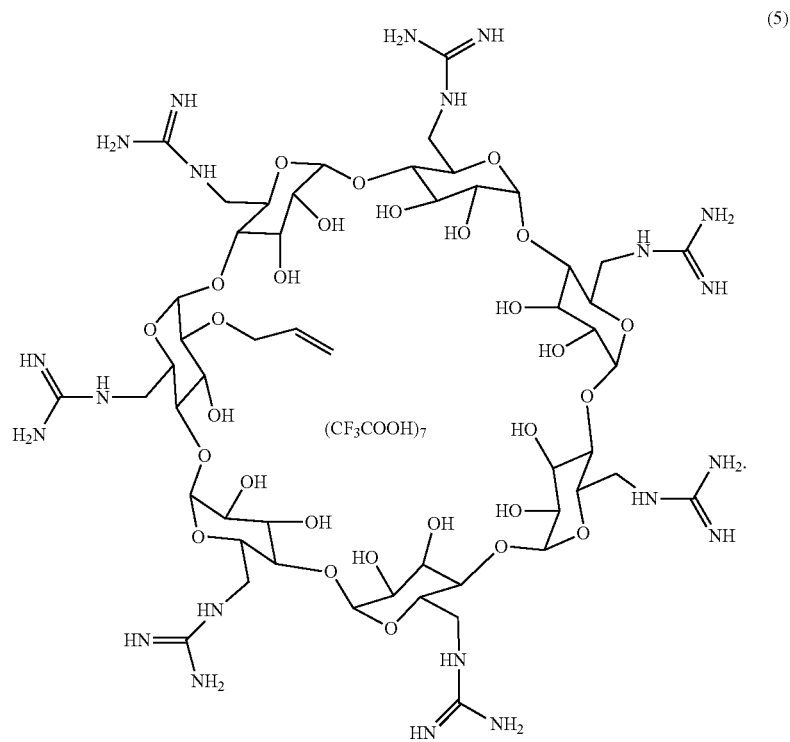
(5)
Compounds 4 and 5 were treated with light of wavelength 365 nm, a photoinitiator 2,2-dimethoxy-2-phenylacetophenon (or azobisisobutyronitrile and heating) and thiols of general formulae SH—(CH$_2$)$_5$—CO-(Arg)$_n$-NH—(CH$_2$)$_2$—NH$_2$ or SH—(CH$_2$)$_5$—CO-(Arg-Aca)$_n$NH$_2$ and converted to compounds of general formula 6,
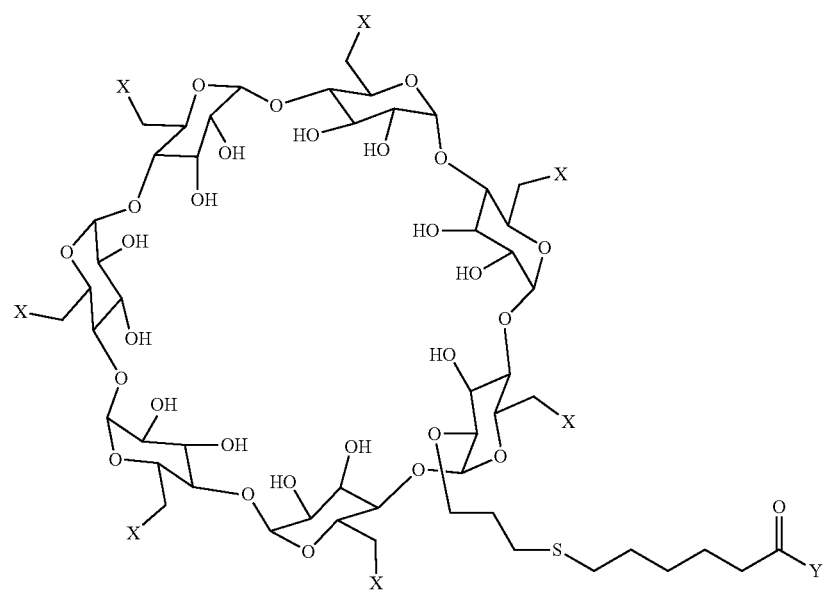
(6)

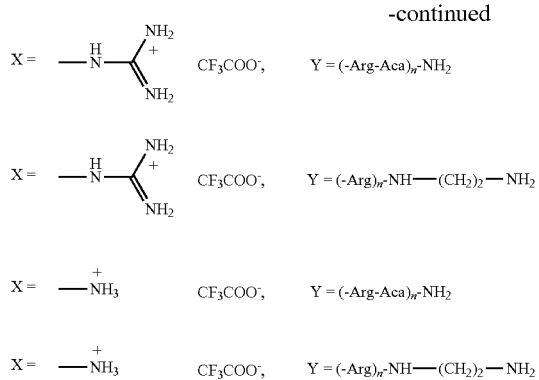

where X is —NH—C(NH$_2$)=N$^+$H$_2$ CF$_3$COO$^-$ or —N$^+$H$_3$ CF$_3$COO$^-$ and Y is a linear oligomer consisting of arginine units terminated with an aminodimethylenamide unit (-Arg)$_n$NH—(CH$_2$)$_2$—NH$_2$, where n=6-10, or arginine-aminocaproic units (-Arg-Aca)$_n$-NH$_2$, where n=6 to 10.

The invention subject also includes a method of the preparation of compounds having general formula 6, where X is —N$^+$H$_3$ CF$_3$COO$^-$ and Y is a linear oligomer consisting of arginine units terminated with an aminodimethylenamide unit (-Arg)$_n$-NH—(CH$_2$)$_2$—NH$_2$, where n=6-10, or arginine-aminocaproic units (-Arg-Aca)$_n$-NH$_2$, where n=6 to 10, which can be prepared more advantageously in such a way that the starting compound 1 is treated with allyl bromide or allyl iodide and sodium hydride or potassium tert-butoxide in dimethylformamide to produce a mixture of 2$^I$-O-allyl-heptakis(6-azido-6-deoxy)-β-cyclodextrin 3 and 3$^I$-O-allyl-heptakis(6-azido-6-deoxy)-β-cyclodextrin 9 in ratio approximately 9:1

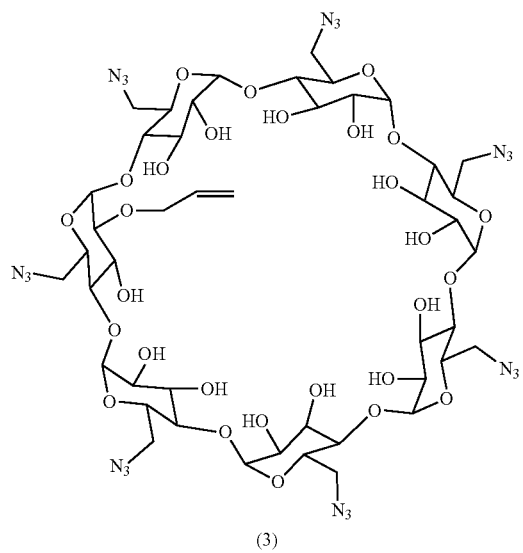

(3)

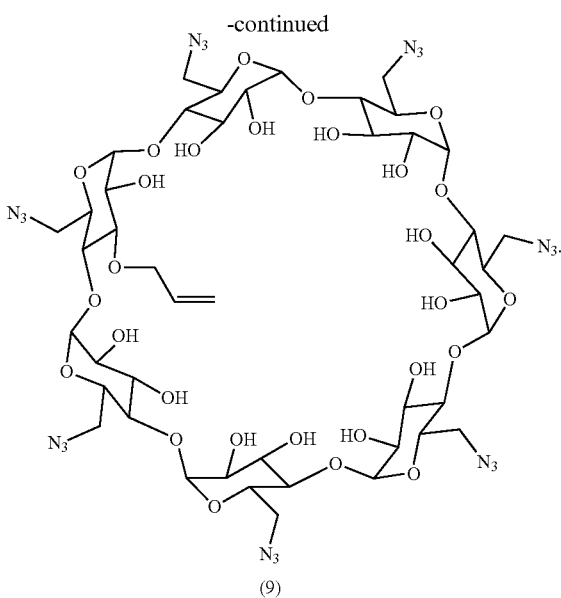

(9)

The mixture of isomeric compounds 3 and 9 is treated with ethyl trifluoroacetate and DIPEA in methanol to produce a mixture of isomeric compounds 10 and 11

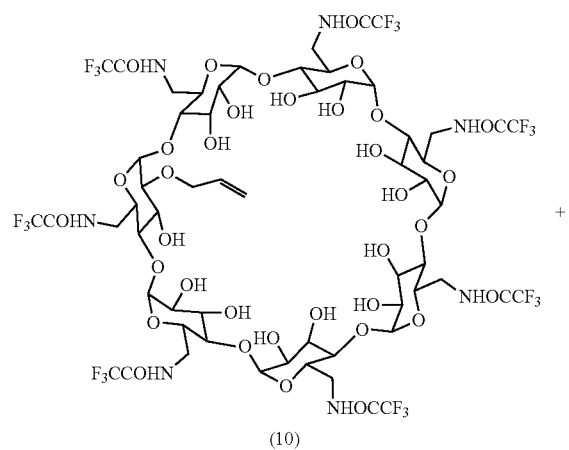

(10)

-continued

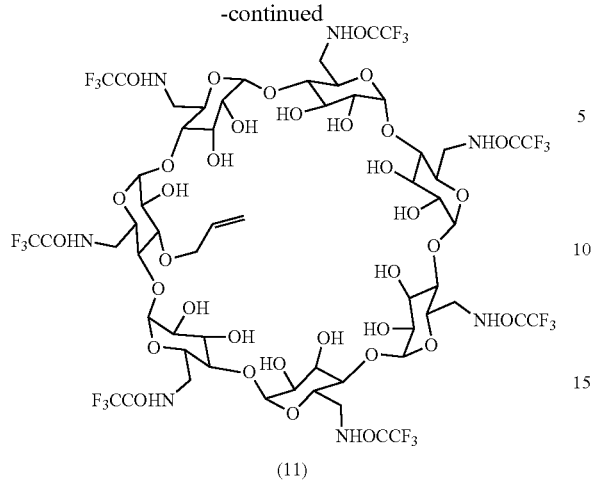

(11)

which are separated by means of reversed-phase HPLC.

Compound 10 is treated with light of wavelength 365 nm, a photoinitiator 2,2-dimethoxy-2-phenylacetophenon (or azobisisobutyronitrile and heating) and thiols of general formulae SH—(CH$_2$)$_5$—COO-(Arg)$_n$-NH—(CH$_2$)$_2$—NH$_2$ or SH—(CH$_2$)$_5$—CO-(Arg-Aca)$_n$-NH$_2$, where n=6-10, and, in this way, converted to compounds of general formula 12, where Y is a linear oligomer consisting of arginine units terminated with an aminodimethylenamide unit (-Arg)$_n$-NH—(CH$_2$)$_2$—NH$_2$, where n=6-10, or arginine-aminocaproic units (-Arg-Aca)$_n$-NH$_2$, where n=6 to 10.

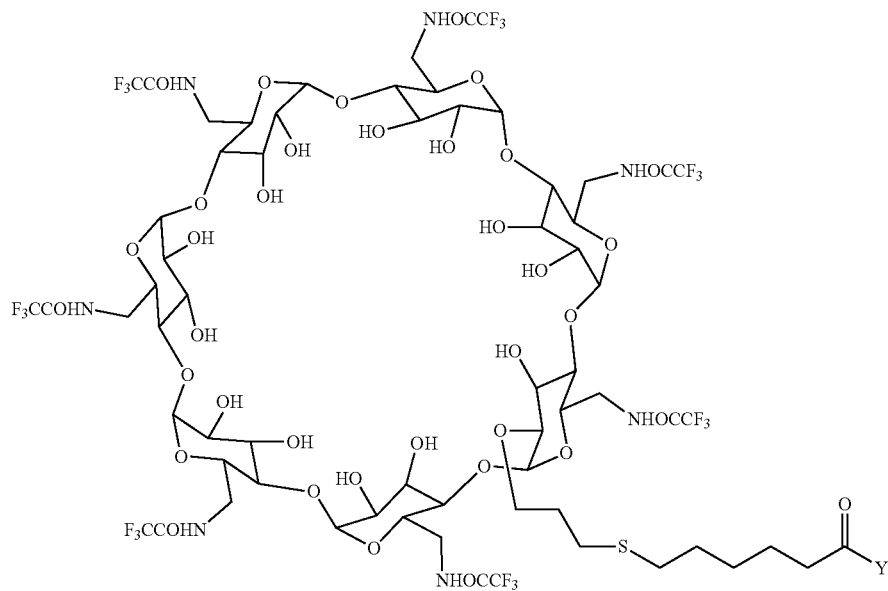

Y = (-Arg-Aca)$_n$-NH$_2$
Y = (-Arg)$_n$-NH—(CH$_2$)$_2$—NH$_2$ (12)

Compounds having general formula 12 are treated with aqueous ammonia to remove protective groups to obtain final products of general formula 6, where X is —N$^+$H$_3$ CF$_3$COO$^-$ and Y is a linear oligomer consisting of arginine units terminated with an aminodimethylenamide unit (-Arg)$_n$-NH—(CH$_2$)$_2$—NH$_2$, where n=6-10, or arginine-aminocaproic units (-Arg-Aca)$_n$-NH$_2$, where n=6 to 10.

The molecular transporters of general formula 6 are more advantageously used with live cells when they are converted to chloride counterion forms by means of passing their aqueous solutions through Dowex-1 ionexchanger prepared in Cl$^-$ form. In this way the potential cytotoxicity of trifluoroacetate anion is avoided.

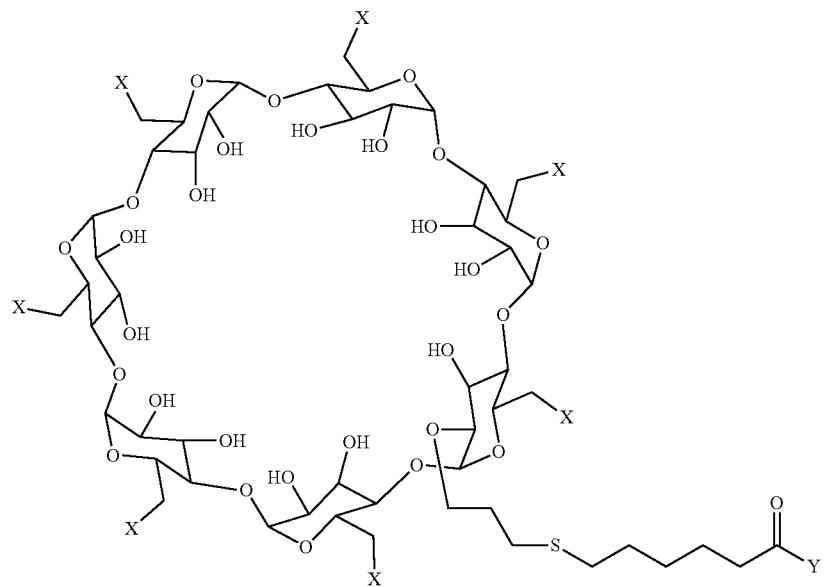
(6)
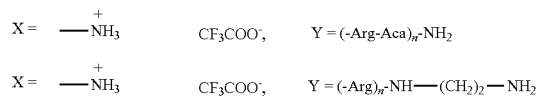
X = —NH₃⁺  CF₃COO⁻,  Y = (-Arg-Aca)ₙ-NH₂
X = —NH₃⁺  CF₃COO⁻,  Y = (-Arg)ₙ-NH—(CH₂)₂—NH₂
The invention subject also includes a method of preparing compounds of general formula 13
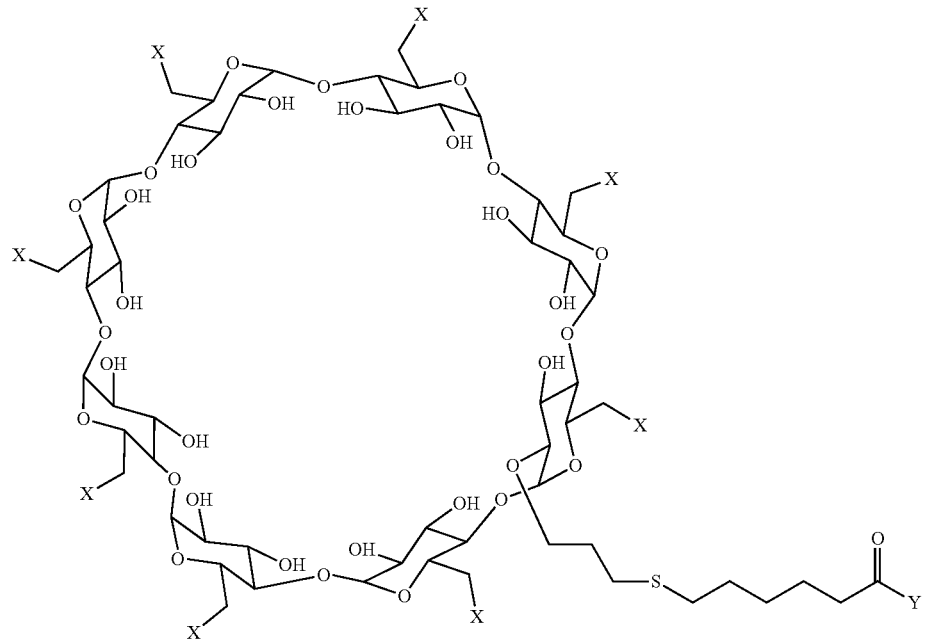
(13)

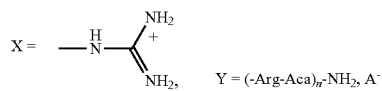
Y = (-Arg-Aca)$_n$-NH$_2$, A$^-$

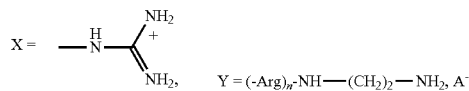
Y = (-Arg)$_n$-NH—(CH$_2$)$_2$—NH$_2$, A$^-$

X = —$\overset{+}{N}$H$_3$,   Y = (-Arg-Aca)$_n$-NH$_2$, A$^-$

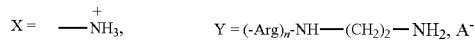
X = —$\overset{+}{N}$H$_3$,   Y = (-Arg)$_n$-NH—(CH$_2$)$_2$—NH$_2$, A$^-$ where X is NHC(NH$_2$)=N$^+$H$_2$ or N$^+$H$_3$ and Y is a linear oligomer consisting of arginine units terminated with an aminodimethylenamide unit (Arg)NH(CH$_2$)$_2$NH$_2$, where n=6-10, or arginine-aminocaproic units (-Arg-Aca)NH$_2$, where n=6 to 10, A$^-$ is CF$_3$COO$^-$ or Cl$^-$; the number of counteranions varies from 10 to 16 per molecule.

Mixture of 2$^I$-O-allyl-octakis(6-azido-6-deoxy)-γ-cyclodextrin 14 and 3$^I$-O-allyl-octakis(6-azido-6-deoxy)-γ-cyclodextrin 15 are prepared from corresponding octakis(6-azido-6-deoxy)-γ-cyclodextrin by a procedure analogous to that described above for the preparation of compounds 3 and 9. Purification by column chromatography yields material containing compound 2$^I$-O-allyl-octakis(6-azido-6-deoxy)-γ-cyclodextrin 14 (≥90%) contaminated with isomer 3$^I$-O-allyl-octakis(6-azido-6-deoxy)-γ-cyclodextrin 15 (≤10%).

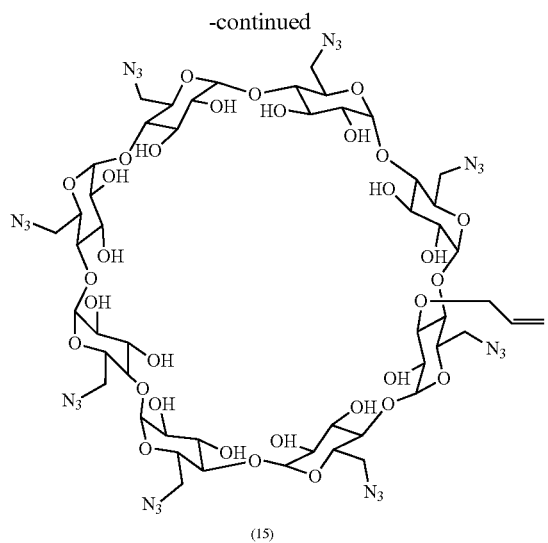
(15)

2$^I$-O-allyl-octakis(6-azido-6-deoxy)-γ-cyclodextrin 14 is reduced to corresponding 2$^I$-O-allyl-octakis(6-amino-6-deoxy)-γ-cyclodextrin 16 by action of triphenylphosphin and aqueous ammonia analogously as described above for the preparation of compound 4.

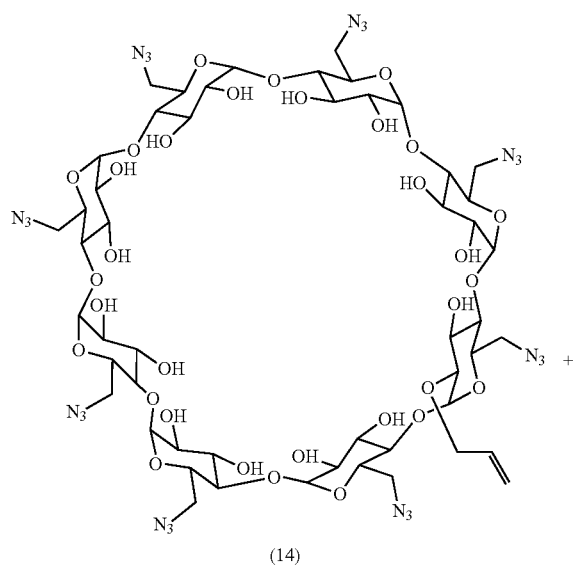
(14)

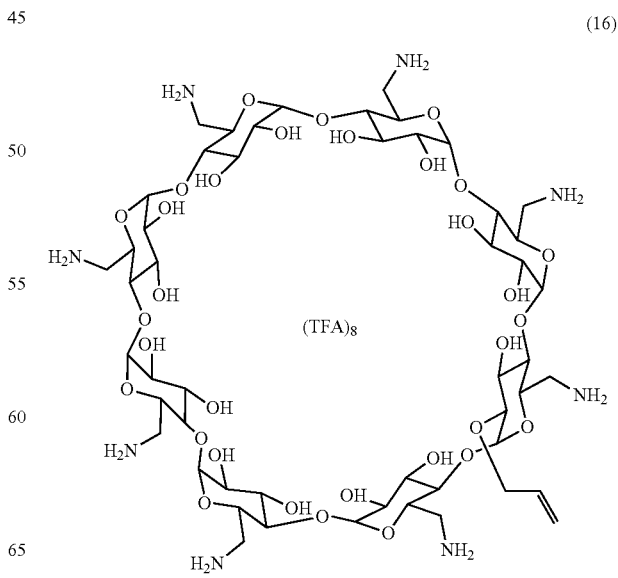
(16)

Compound 16 is treated with 1H-pyrazole-1-carboxamidine hydrochloride and converted to 2′-O-allyl-octakis(6-guanidino-6-deoxy)-γ-cyclodextrin octakis (trifluoroacetate) of structural formula 17.

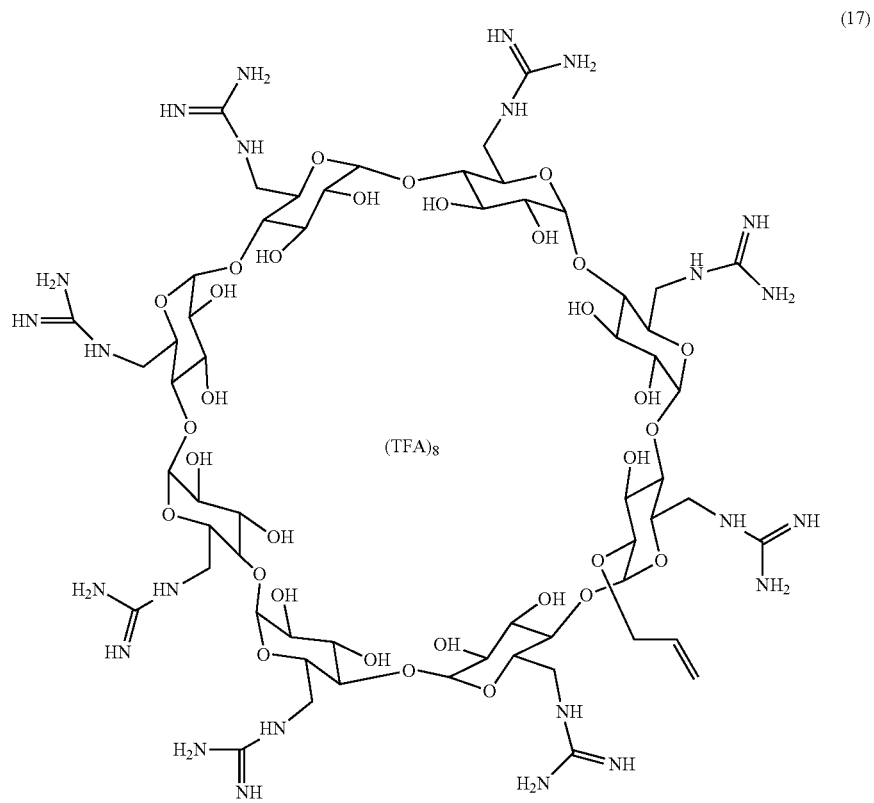 [SMILES: C=CCOC1C2OC(CNC(=N)N)C(OC3OC(CNC(=N)N)C(OC4OC(CNC(=N)N)C(OC5OC(CNC(=N)N)C(OC6OC(CNC(=N)N)C(OC7OC(CNC(=N)N)C(OC8OC(CNC(=N)N)C(OC9OC(CNC(=N)N)C(O2)C(O)C9O)C(O)C8O)C(O)C7O)C(O)C6O)C(O)C5O)C(O)C4O)C(O)C3O)C1O ; "(TFA)8"]

Compounds 16 and 17, respectively, are treated with light of wavelength 365 nm, a photoinitiator 2,2-dimethoxy-2-phenylacetophenon (or azobisisobutyronitrile and heating) and thiols of general formulae SH—(CH$_2$)$_5$—CO-(Arg)$_n$-NH—(CH$_2$)$_2$—NH$_2$ or SH(CH$_2$)$_5$—CO-(Arg-Aca)$_n$-NH$_2$ and converted to compounds of general formula 13,

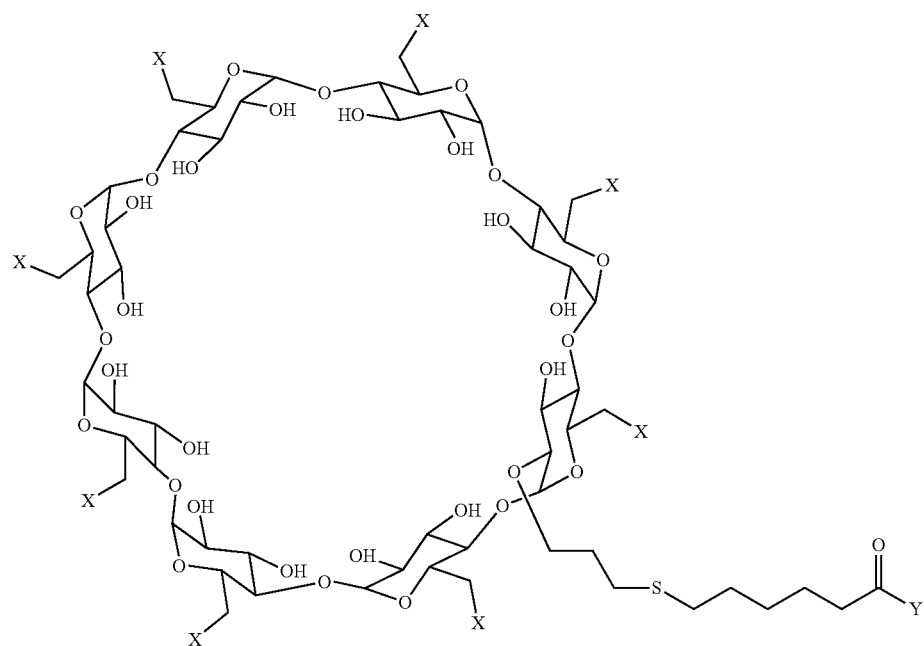

X = 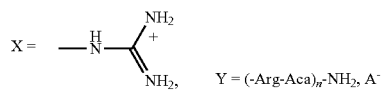, Y = (-Arg-Aca)$_n$-NH$_2$, A$^-$

X = 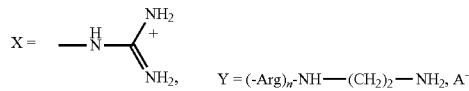, Y = (-Arg)$_n$-NH—(CH$_2$)$_2$—NH$_2$, A$^-$

X = —NH$_3^+$, Y = (-Arg-Aca)$_n$-NH$_2$, A$^-$

X = 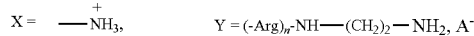—NH$_3^+$, Y = (-Arg)$_n$-NH—(CH$_2$)$_2$—NH$_2$, A$^-$ where X is —NH—C(NH$_2$)=N$^+$H$_2$ or —N$^+$H$_3$ and Y is a linear oligomer consisting of arginine units terminated with an aminodimethylenamide unit (-Arg)$_n$-NH—(CH$_2$)$_2$—NH$_2$, where n=6-10, or arginine-aminocaproic units (-Arg-Aca)$_n$-NH$_2$, where n=6 to 10, A$^-$ is CF$_3$COO$^-$ or Cl$^-$; the number of counteranions varies from 10 to 16 per molecule.

Subject of the invention further includes the use of compounds of general formulae 6 and 13 as carriers of NTPs across cell membranes, preferably for incorporation of the NTP into the cellular DNA or RNA. A solution of the compound of formula 6 in an aqueous buffer having the composition shown below was mixed with the NTP so that the carrier and NTP concentration was higher than 1 µmol·l$^{-1}$ and the resulting complex is applied to the cell culture for a period of 1-60 min. Confocal microscopy and cytometry demonstrated that NTP permeates through the cell membrane as early as within the first minute after exposure, and concentrates in the nucleus. Monitoring over a longer time interval showed selective fluorescence of chromosomal DNA of dividing cells.

The subject of invention further includes the use of compounds of formulae 6 and 13 as carriers of nucleoside triphosphates across the cell membrane for the purpose of determining the virostatic activities of modified NTPs. Cell culture infected with a virus is shortly (1-30 min) exposed to the solution of the complex of modified NTPs and compounds of general formula 6 and thus treated cells are then incubated according to standard procedures. Virostatic activity evaluation is made by comparing with a control experiment in which the standard is present in the medium throughout the incubation. This eliminates negative results caused by the lack of phosphorylation of the nucleoside investigated by cellular kinases.

The subject of the invention further includes the use of compounds of formulae 6 and 13 as carriers of nucleoside triphosphates across the cell membranes for the purpose of testing proliferation activity (S-phase cell cycle progression) of living cells, which are nowadays performed with "BrdU" or "Click-it-EdU" protocols (Click-it-EdU is registered trademark of an assay commercialized by Invitrogen, ThermoFisher Scientific). With advantageous use of NTP transporters, i.e. compounds of formulae 6 and 13, a fluorescently labeled NTP analog is translocated to intracellular milieu of living cells, where it is incorporated to DNA, which can be immediately visualized by fluorescence detection without the need of post-labeling required by standard protocols. This new procedure is significantly operationally more simple as compared to standard "BrdU" or "Click-it-EdU" protocols. Thus, cell culture is treated with the complex of fluorescently labelled deoxy-NTP (capable of incorporation to DNA by natural polymerases) with a transporter in a buffer for a short period of time (1-15 min). Then the complex is washed out and the cells are incubated in a standard medium allowing for DNA replication for a requested period of time (1 min-24 hod), after which the cells are harvested, the membranes are permeabilized and analysed by means of flow cytometry or, alternatively, treated with a secondary staining agent (detection of live/dead cells, quantifying DNA etc.) exhibiting fluorescence with a wavelength not interfering with NTP, prior to flow cytometry analysis.

Counterions A$^-$ independently represent anions of salts, in particular of pharmaceutically acceptable salts.

The salts include salts with inorganic or organic anions and in particular, but not exclusively, pharmaceutically acceptable salts suitable for physiological application. Pharmaceutically acceptable salts can be salts derived from inorganic or organic acids. Expert in the field will be able to determine, which salts are pharmaceutically acceptable; especially salts having one or more favourable physico-chemical characteristic such as longer pharmaceutical stability at various temperatures and humidities, desired solubility in water or oil, or are not toxic.

Suitable pharmaceutically acceptable salts of the compounds according to this invention preferably include anions derived from inorganic acids such as hydrochloric acid, hydrobromic acid, hydrofluoric acid, boric acid, phosphoric acid, metaphosphoric acid, nitric acid, carbonic acid, sulfurous acid, sulphuric acid; and organic acids such as acetic acid, benzenesulfonic acid, benzoic acid, citric acid, ethanesulfonic acid, fumaric acid, gluconic acid, glycolic acid, isethionic acid, lactic acid, laktobionic acid, maleic acid, malonic acid, methanesulfonic acid, trifluoromethanesulfonic acid, succinic acid, toluenesulfonic acid, tartaric acid, and trifluoroacetic acid. Suitable organic acids generally encompass for example the following classes of organic acids: aliphatic, cycloaliphatic, aromatic, arylaliphatic, heterocyclic, carboxylic and sulfonic acids.

Specific examples of suitable organic acid salts include acetate, trifluoroacetate, formate, propionate, succinate, glycolate, gluconate, digluconate, lactate, malate, tartrate, citrate, ascorbate, glucuronate, maleate, fumarate, pyruvate, aspartate, glutamate, benzoate, anthranilate, stearate, salicylate, p-hydroxybenzoate, phenylacetate, mandelate, pamoate, methanesulfonate, ethanesulfonate, benzenesulfonate, pantothenate, toluenesulfonate, 2-hydroxyethanesulfonate, sulfanilate, cyclohexylaminosulfonate, 3-hydroxybutyrate, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalenesulfonate, oxalate, palmoate, pectinate, 3-phenylpropionate, picrate, pivalate, thiocyanate and undecanoate.

In some embodiments are disclosed compounds of general formula 6 or 13, where Y is an oligomer having linear or branched or cyclic arrangement or any combination of these, consisting of 5-12, preferably 6-10 arginine units which can be separated by 0-4 spacers chosen from a group, comprising amino acids, polyethylene glycol units, $C_1$-$C_{16}$ alkyl, $C_3$-$C_{16}$ cycloalkyl, $C_1$-$C_{16}$ alkenyl, $C_3$-$C_{16}$ cycloalkenyl $C_1$-$C_{16}$ alkynyl $C_4$-$C_{14}$ aryl or $C_4$-$C_{14}$ heteroaryl, or any other organic moiety in between each or selected arginine units, so that the distance between subsequent arginine units does not exceed 20 atoms and the total length of all spacers does not exceed 100 atoms.

Alkyl is a linear or branched $C_1$-$C_{16}$, preferably $C_2$-$C_{12}$, most preferably $C_2$-$C_8$ hydrocarbon chain;

alkenyl is a linear or branched $C_2$-$C_{16}$, preferably $C_2$-$C_{12}$, most preferably $C_2$-$C_8$ hydrocarbon chain comprising at least one double bond, alkynyl is a linear or branched $C_2$-$C_{16}$, preferably $C_4$-$C_{12}$, most preferably $C_4$-$C_8$ hydrocarbon chain comprising at least one triple bond, which can optionally comprise also a double bond;

cycloalkyl is a linear or branched $C_3$-$C_{16}$, preferably $C_3$-$C_{10}$, most preferably $C_3$-$C_6$ hydrocarbon chain comprising at least one cycle;

cycloalkenyl is a linear or branched $C_3$-$C_{16}$, preferably $C_4$-$C_{10}$, most preferably $C_4$-$C_6$ hydrocarbon chain comprising at least one double bond;

aryl is a hydrocarbon group comprising 6-14 carbon atoms, preferably 6-12 carbon atoms, and comprising at least one aromatic cycle;

heteroaryl is a hydrocarbon group comprising 2-14 carbon atoms, preferably 4-10 carbon atoms and at least one heteroatom, preferably 1-2 heteroatoms selected from a group comprising O, S, N, and comprising at least one aromatic cycle.

In certain embodiments some or all arginine units in compounds of general formula 6 or 13 may be replaced with naturally occurred amino acids containing guanidine moiety or guanidino peptidomimetics chosen from norarginine, homoarginine and β-homoarginine. In certain embodiments some or all amido groups in compounds of general formula 6 or 13 may be replaced by different functional groups chosen from ester group, amine group, carbamate group or ether group.

BRIEF DESCRIPTION OF FIGURES

FIG. 5: a) Monitoring the penetration of a complex of compound 6a and fluorescently labelled NTP (ChromaTide® Alexa Fluor® 488-5-dUTP; ThermoFisher Scientific, Cat. No.: C11397) into U2-OS cells; b) control experiment performed by applying NTP to the cell culture (ChromaTide® Alexa Fluor® 488-5-dUTP; ThermoFisher Scientific, Cat. No.: C11397) without compound 6a.

FIG. 10: Chemical shifts of $^1$H NMR (ppm) in the spectra of compounds 2-5, 10 and 14. Spectra were taken at a frequency of 600 MHz.
FIG. 11: Chemical shifts of $^{13}$C NMR (ppm) in the spectra of compounds 2-5, 10 and 14. Spectra were taken at a frequency of 151 MHz.

Figure 1:
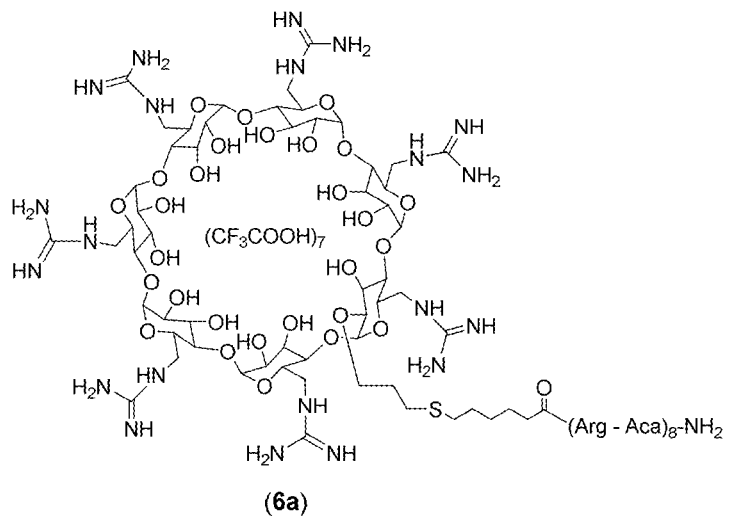
FIG. 1: Structural formula of Conjugate 6a
FIG. 2: Structural formula of Conjugate 6b

The invention will be further illustrated by the following examples, however, it is not restricted only to these.

EXAMPLES OF THE INVENTION EMBODIMENT

List of Abbreviations

ACN Acetonitrile
AcOEt Ethyl acetate
BrdU 5-Bromo-2-deoxyuridine
DIPEA N,N-Diisopropylethylamin
EtOH Ethanol
HRMS High Resolution Mass Spectroscopy
MALDI Matrix-assisted laser desorption/ionization
NMR Nuclear magnetic resonance
NTP Nucleoside triphosphate
TBME tert-Butyl methyl ether
TFA Trifluoroacetic acid
THF Tetrahydrofurane
HPLC High performance liquid chromatography
DNA Deoxyribonucleic acid
LED Light-emitting diode
HIV Human immunodeficiency virus
Aminoallyl-dUTP—Cy3 5-(3-Aminoallyl)-2'-deoxyuridin-5'-triphosphate, bearing the Cy3 fluorescent label
Cy3 Cyanine fluorophore
TZM-bl Cell lines of cervical cancer
DMF N,N-Dimethylformamide
MeOH Methanol
U2-OS Human osteosarcoma cell line

Example 1

Preparation of $2^{II\text{-}VII},3^{I\text{-}VII}$-trideca-O-acetyl-$2^I$-mono-O-allyl-$6^{I\text{-}VII}$-hepta-azido-$6^{I\text{-}VII}$-hepta-deoxy-β-cyclodextrin 2

Sodium hydride free of oil (54.8 mg, 2.28 mmol) was added to a solution of compound 1 (2 g, 1.52 mmol) in anhydrous dimethylformamide (40 ml) and reaction mixture was stirred for 3 hours at room temperature under an argon atmosphere. Allyl bromide (200 µl, 2.30 mmol) was then dropwise added to the reaction mixture and the mixture was allowed to react for 12 hours. Then, dimethylformamide was evaporated and the product mixture purified by column chromatography (silica gel, chloroform, methanol 4:1); and the fraction containing isomers $2^I$-O-allyl-heptakis(6-azido-6-deoxy)-β-cyclodextrin and $3^I$-O-allyl-heptakis(6-azido-6-deoxy)-β-cyclodextrin (total 740 mg) was isolated. This mixture (600 mg, 0.44 mmol) was dissolved in acetonitrile (18 ml) and acetanhydride (1 ml, 10.57 mmol), N,N-diisopropylethylamin (3 ml, 17.22 mmol) and N,N-dimethylaminopyridine (70 mg, 0.57 mmol) were gradually added to the solution with stirring. The reaction mixture was stirred for 12 hours at room temperature, then evaporated on a rotary evaporator and the residue was suspended in chloroform (100 ml) and the resulting suspension was washed with water (3×50 ml). The chloroform layer was dried with sodium sulphate, then the desiccant was removed by filtration on sintered glass and the resulting solution was concentrated to a volume of about 10 ml and loaded on a chromatographic column (silica gel, chloroform/acetone 5:1). The main fraction after evaporation contained $2^I$-O-allyl-heptakis(6-azido-6-deoxy)-O-cyclodextrin 2 (702 mg, 31%).

Characterization: HRMS (MALDI): m/z calculated for $C_{71}H_{93}N_{21}O_{41}$ [M+Na]$^+$: 1918.5730; found 1918.5758; elemental analysis (%): calculated for $C_{71}H_{93}N_{21}O_{41}$: C, 44.96; H, 4.94; N, 15.51; found C, 44.98; H, 4.92; N, 15.41. $^1$H and $^{13}$C NMR data—see FIGS. 10 and 11.

Example 2

Preparation of $2^I$-O-allyl-heptakis(6-azido-6-deoxy)-β-cyclodextrin 3

Compound 2 (700 mg, 0.369 mmol) was dissolved in sodium methanolate solution in anhydrous methanol (0.1 mol·l$^{-1}$, 70 ml). The reaction mixture was stirred at room temperature; formation of a white precipitate was observed during the reaction. After 3 hours, the mixture was evaporated to dryness, the residue was dissolved in a mixture of methanol and dimethylformamide 1:1 (2 ml) and re-precipitated with water (100 ml). The precipitate was filtered on a sintered glass and dried under vacuum at room temperature. Compound 3 was isolated in a yield of 375 mg (75%).

Characterization: HRMS (MALDI): m/z calculated for $C_{45}H_{67}N_{21}O_{28}$ [M+Na]$^+$: 1372.4357; found 1372.4362; elemental analysis (%: calculated for $C_{45}H_{67}N_{21}O_{28}$: C, 40.03; H, 5.00; N, 21.79; found C: 41.59; H, 5.44; N, 18.42. $^1$H and $^{13}$C NMR data—see FIGS. 10 and 11.

Example 3

Preparation of $2^I$-O-allyl-heptakis(6-amino-6-deoxy)-β-cyclodextrin heptakis(trifluoroacetate) 4

Triphenylphosphine (190 mg, 0.72 mmol) was added to a solution of compound 3 (70 mg, 0.05 mmol) in dimethylformamide (1.4 ml). After 2 hours a solution of ammonia in water (0.5 ml of 25% solution) was added to the reaction mixture and the mixture was stirred for 16 h. The solvent was then evaporated and acetone (20 ml) was added to the resulting thick syrup. The resulting white precipitate was isolated by filtration on sintered glass and then suspended in a mixture of methanol (1.5 ml) and ammonia (1.5 ml). The mixture was heated in a pressure tube at 60° C. for 6 hrs, and then evaporated under reduced pressure. The residue was dissolved in a 0.01% aqueous solution of trifluoroacetic acid and purified by ultrafiltration on a membrane with 1 kDa pores (Ultracell; manufacturer Merck Millipore), and lyophilized. The yield of compound 4 was 53 mg (48%).

Characterization: HRMS (MALDI): m/z calculated for $C_{45}H_{67}N_7O_{28}$ [M+Na]$^+$: 1190.5022; found 1190.5036; elemental analysis (%), calculated for $C_{45}H_{67}N_7O_{28}$.7TFA.5H$_2$O: C, 34.46; H, 4.80; N, 4.77; found C, 34.42; H, 4.80; N, 4.37. $^1$H and $^{13}$C NMR data—see FIGS. 10 and 11.

Example 4

Preparation of $2^I$-O-allyl-heptakis(6-guanidino-6-deoxy)-β-cyclodextrin heptakis(trifluoroacetate) 5

Compound 4 (35 mg, free base) and 1H-pyrazolcarboxamidin hydrochloride (219 mg) were suspended in a mixture of N,N-diisopropylethylamine (0.26 ml) and water (0.26 ml). The mixture was stirred at room temperature for 24 hours, then solvents were evaporated under reduced pressure. The residue was dissolved in a 0.01% aqueous solution of trifluoroacetic acid and purified by ultrafiltration on a membrane with 1 kDa pores (Ultracell; manufacturer Merck Millipore), and lyophilized. Yield of compound 5 was 33 mg (49%).

Characterization: HRMS (MALDI), m/z calculated for $C_{52}H_{96}N_{21}O_{28}$ [M+H]$^+$: 1462.6728; found 1462.6758; elemental analysis (%), calculated for $C_{66}H_{102}F_{21}N_{21}O_{42}$.7TFA.6H$_2$O C; 33,47; H; 4.85; F; 16.84; N; 12.42; O; 32.42 $^1$H a $^{13}$C NMR data—see FIGS. 10 and 11.

Example 5

Synthesis of Conjugate 6a (FIG. 1)

2,2-Dimethoxy-2-phenylacetophenone (0.89 mg), SH—(CH$_2$)$_5$—CO-(Arg-Aca)$_8$-NH$_2$ thiol (44.90 mg; prepared by standard peptide solid phase synthesis using an automated ABI 433A synthesizer, Applied Biosystems) and the compound of formula 5 (34.7 mg) were dissolved in DMF. The mixture was stirred with ultrasound followed by magnetic stirring under an inert atmosphere of argon. The mixture was periodically irradiated with UV light of wavelength 365 nm generated by the LED (1 W) under constant stirring for 1 min, then the mixture was allowed to stand for 20 min; the process was repeated 6 times. The reaction mixture was monitored by HPLC after each irradiation cycle. After completion of the reaction, the product was precipitated with 10 ml of AcOEt, filtered on sintered glass and washed with AcOEt (3×0.5 ml). The crude product was dried, then dissolved in 15% ACN in water and lyophilised. The compound was purified by HPLC on a Phenomenex Gemini column 5 μm NX-C18 250×21.2 mm (manufacturer Phenomenex®); linear gradient A and B: 7-18% B in 14 min, 100% B in 15 min; 14 ml/min; 25° C.; where A was a 0.02% solution of TFA in water and B was 100% ACN. Yield of the compound: 27.8 mg (36%).

Characterization: HRMS (MALDI): for $C_{154}H_{293}N_{62}O_{45}S$ [M+H]$^+$ calculated 3763.226; found 3763.231; analytical HPLC: column ZORBAX Poroshell 120 SB-C18; 3×50 mm (manufacturer Agilent); 2.7 μm; linear gradient A and B: 0.5% B 0-1 min, then linear gradient up to 22% B during 10 min; 1 ml/min; 25° C.; where A was 0.05% TFA in water, B was 100% ACN. Retention time of compound 6a=8.6 min.

Example 6

Figure 2:
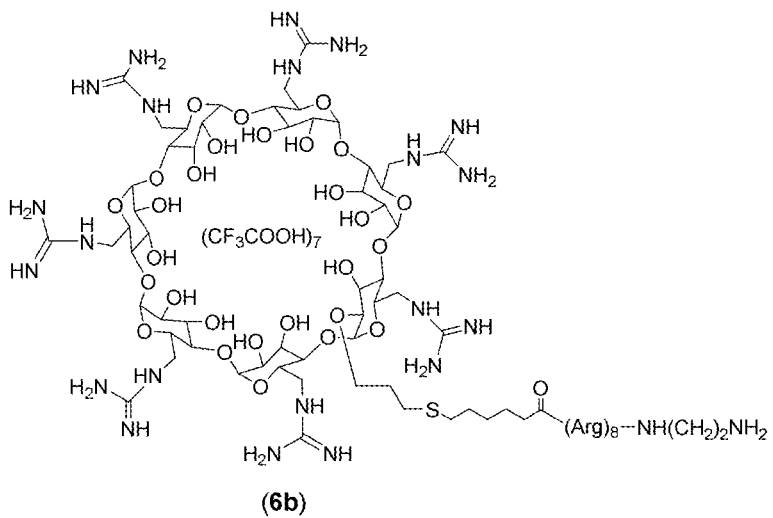

Synthesis of Conjugate 6b (FIG. 2)

Compound 6b was prepared analogously to the above described compound 6a using 2,2-dimethoxy-2-phenylacetophenone (0.12 mg), thiol SH—(CH$_2$)$_5$—CO-(Arg)$_8$-NH—(CH$_2$)$_2$—NH$_2$ (2.32 mg; prepared by standard peptide synthesis on a solid phase using an automatic ABI 433A synthesizer, Applied Biosystems) and compound 5 (5.58 mg). Yield 1.60 mg (36%).

Characterization: HRMS (MALDI): for $C_{108}H_{210}N_{55}O_{37}S$ [M+H]$^+$ calculated 2901.596; found 2901.595; analytical HPLC: column ZORBAX Poroshell 120 SB-C18; 3×50 mm (manufacturer Agilent); 2.7 μm; linear gradient A and B: from 5% B to 20% B over 5 min; 1 ml/min; 25° C.; where A was a 0.02% solution of TFA in water, B was 100% ACN. Retention time of compound 6b=2.6 min.

Example 7

Figure 3:
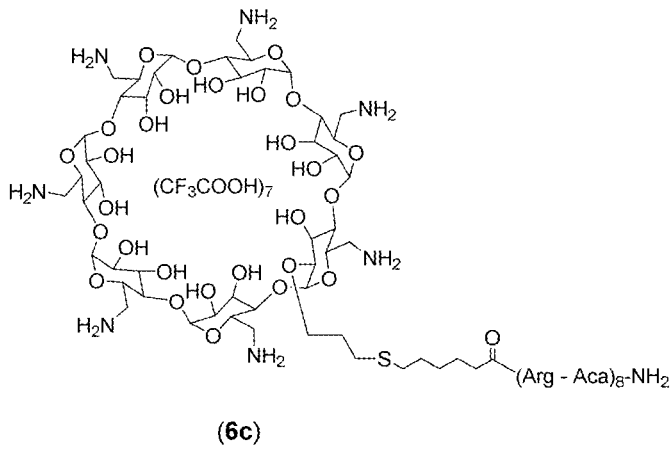
FIG. 3: Structural formula of Conjugate 6c

Synthesis of Conjugate 6c (FIG. 3)

Compound 6c was prepared analogously to the above described compound 6a using 2,2-dimethoxy-2-phenylacetophenone (0.84 mg), thiol SH—$(CH_2)_5$—CO-(Arg-Aca)$_8$-$NH_2$ (29.3 mg; prepared by standard peptide synthesis on a solid phase using an automatic ABI 433A synthesizer, Applied Biosystems) and compound 4 (44.1 mg). Yield 17.4 mg (39%). Characterization: HRMS (MALDI): for $C_{147}H_{279}N_{48}O_{45}S$ [M+H]$^+$ calculated 3469.073; found 3469.070; analytical HPLC: column ZORBAX Poroshell 120 SB-C18; 3×50 mm (manufacturer Agilent); 2.7 µm; linear gradient A and B: from 5% B to 20% B over 5 min; 1 ml/min; where A was a 0.02% solution of TFA in water, B was 100% ACN. Retention time of compound 6c=3.7 min.

Example 8

Figure 4:
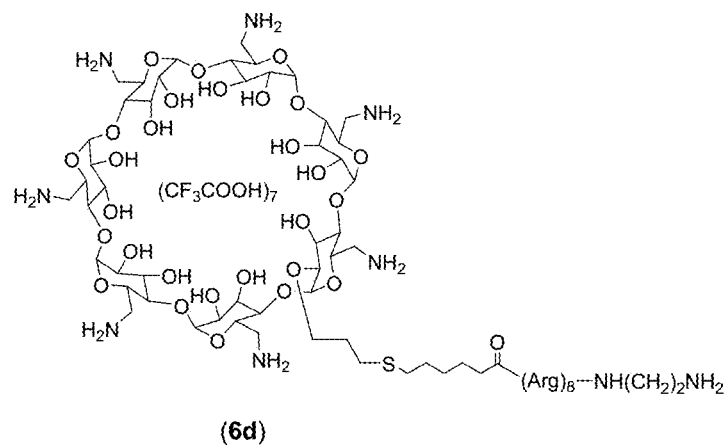
FIG. 4: Structural formula of Conjugate 6d

Synthesis of Conjugate 6d (FIG. 4)

Compound 6d was prepared analogously to above described compound 6a using 2,2-dimethoxy-2-phenylacetophenone (0.13 mg), thiol SH—$(CH_2)_5$—CO-(Arg)$_8$-NH—$(CH_2)_2$—$NH_2$ (2.22 mg; prepared by standard peptide synthesis on a solid phase using an automatic ABI 433A synthesizer, Applied Biosystems) and compound 4 (7.62 mg). Yield 1.38 mg (35%).

Characterization: HRMS (MALDI): for $C_{101}H_{196}N_{41}O_{37}S$ [M+H]$^+$ calculated 2607.443; found 2607.448; analytical HPLC: column ZORBAX Poroshell 120 SB-C18; 3×50 mm (manufacturer Agilent); 2.7 µm; linear gradient A and B: from 5% B to 20% B over 5 min; 1 ml/min; where A was a 0.02% solution of TFA in water, B was 100% ACN. Retention time of compound 6d=2.2 min.

Example 9

Transport of Nucleoside Triphosphate Carrying a Fluorescent Marker Into U2-OS Cells Preparation of buffer A for application of the complexes: The compounds N-[tris(hydroxymethyl)methyl]glycin (448.14 mg), calcium chloride (100.6 mg), magnesium sulfate (48.8 mg), potassium chloride (200.0 mg), glucose (1.001 g) and sodium chloride (3.661 g) were successively dissolved in 497 ml of deionized sterile water. The acidity of the resulting solution was adjusted with 1 mol·l$^{-1}$ solution of sodium hydroxide to pH 7.40 at 31° C. The solution was made up to 500.0 ml.

Figure 5:
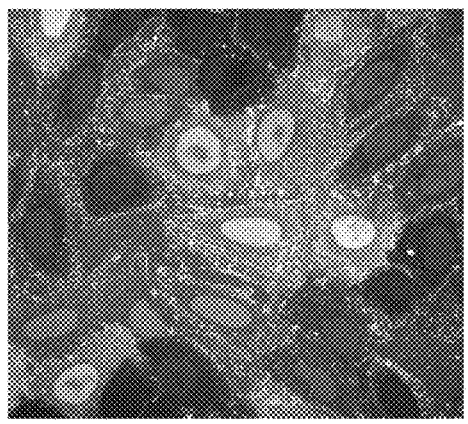
Figure 5:
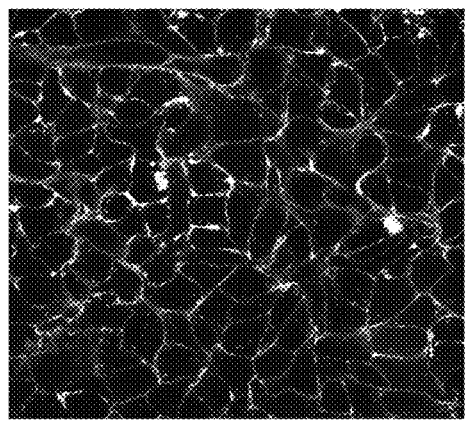

Compound 6a was dissolved in a buffer solution A to a concentration of 20 µmol·l$^{-1}$. Nucleoside triphosphate (ChromaTide® Alexa Fluor® 488-5-dUTP; ThermoFisher Scientific, Cat. No.: C11397) was also dissolved in a solution of buffer A to a concentration of 20 µmol·l$^{-1}$. The solutions were then mixed in equal volume ratios (1:1) to a final concentration of the complex 10 µmol·l$^{-1}$. U2-OS cell culture prepared in a standard manner with 50-100% confluency was shortly washed with buffer A and then the cells were overlaid with the solution of the prepared complex. The sample thus prepared was immediately placed in a confocal microscope and NTP penetration into the cell was monitored at regular time intervals. Colouring of cytosol and nucleus could be observed from the first minute after beginning of observation. Fluorescence was observed in all the cells with varying intensity (FIG. 5a). In a control experiment, where 10 µM solution of NTP alone (ChromaTide® Alexa Fluor® 488-5-dUTP), without compound 6a was applied (FIG. 5b) no penetration of NTP into cells was observed, the presence of NTP was only observed in the intercellular space.

Example 10

Figure 6:
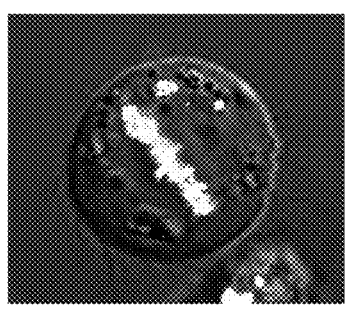
FIG. 6: Monitoring mitosis of U2-OS cells, which achieved incorporation of the fluorescent NTP into genomic DNA (light areas in the figures) with the help of compound 6b and NTP (Aminoallyl-dUTP-Cy3; Jena Bioscience, Cat. No. NU-803-S-Cy3).
Figure 6:
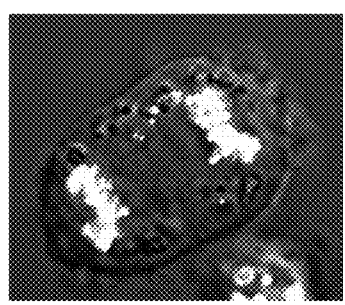
Figure 6:
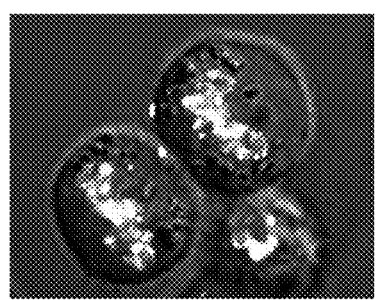

Monitoring of Incorporation of Labeled NTP (Aminoallyl-dUTP-Cy3, Jena Bioscience) Into the DNA Complex of compound 6b and NTP (Aminoallyl-dUTP-Cy3, Jena Bioscience, Cat. No. NU-803-Cy3-S) in buffer A at a final concentration of 25 µmol·l$^{-1}$ was applied to TZM-bl cell culture and incubated for 3 minutes. Then, the solution of the complex was removed from the cells and the cells were overlaid with complete medium, further incubated at 37° C. for 24 hours and periodically monitored by confocal microscopy. Fluorescence of chromosomal DNA of dividing cells (FIG. 6) shows that fluorescently labelled NTP has been incorporated into the genomic DNA of the cells.

Example 11

Testing Virostatic Activity of Adefovir Diphosphate 8

Figure 7:
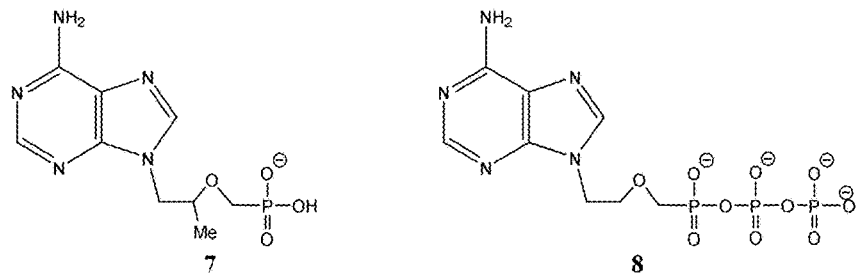
FIG. 7: Graph showing the dependence of the number of viral particles (corresponding to relative fluorescence) on the concentration of substances applied to the cell culture.
Figure 7:
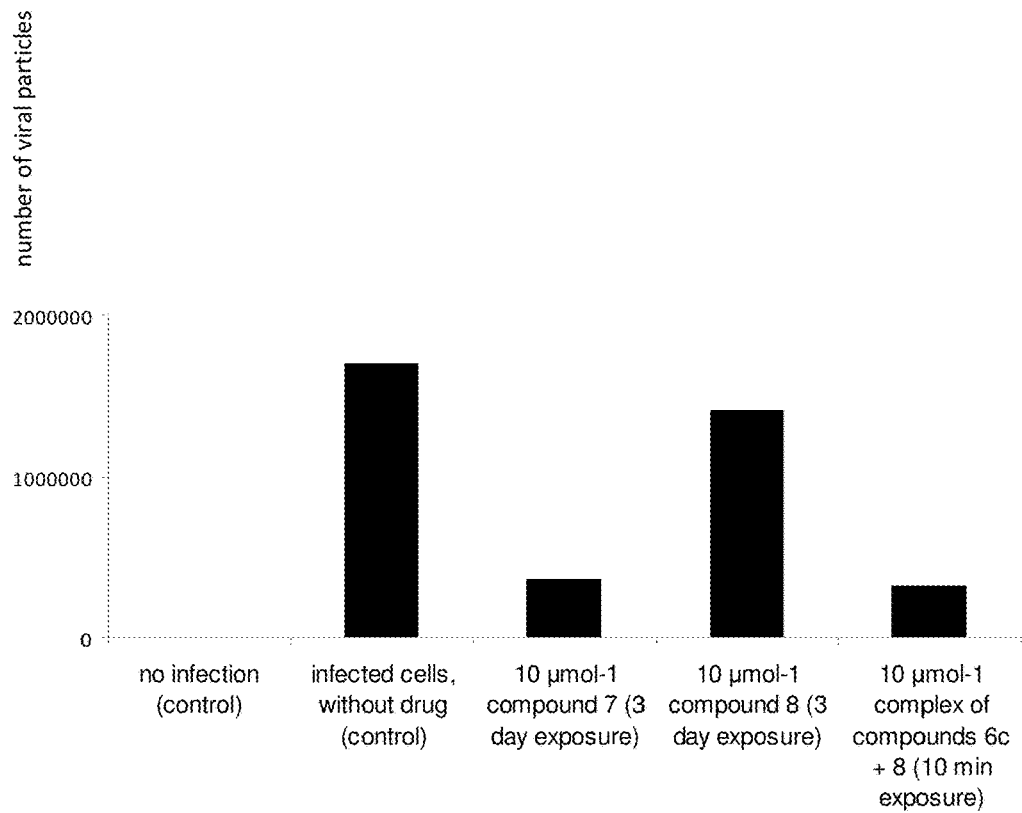

The subject of testing was the compound of structure formula 8 (adefovir diphosphate) which is a known (Mulato & Cherrington, 1997) active metabolite—the reverse transcriptase inhibitor—in inhibiting the replication of viral DNA of HIV. In determining activity of triphosphate 8, compound 7 (tenofovir), which is a clinically approved drug used for the treatment of HIV, was used as a standard. TZM-bl cell culture infected with HIV was exposed to the effect of a solution of 10 µmol·l$^{-1}$ complex of the compound 8 and the transporter—compound 6c—in buffer A for 10 minutes. Then the solution of the complex was removed and the infected cells were overlaid with medium with serum and incubated at 37° C. Parallel control experiments were performed (without infection; infection without active substance; 10 µmol·l$^{-1}$ tenofovir 7 throughout incubation; compound 8 without a carrier). After three days of incubation, virostatic activity of compound 8, transported by 6c for 10 min, was observed—identical with the control experiments where a solution of compound 7 was present in the medium throughout the incubation (FIG. 7). From this observation it may be concluded that compound 8, when applied as the active metabolite (triphosphate) using the 6c carrier is—due to the much shorter time of application—more active than the clinically used drug 7, used here as a standard.

Example 12

Preparation of 2$^I$-O-allyl-heptakis(6-trifluoroacetamido-6-deoxy)-β-cyclodextrin 10

Triphenylphosphine (141 mg, 0.53 mmol) was added to a solution of isomers 3 and 9 (52 mg, 0.038 mmol) in dimethylformamide (1.04 ml). After 2 hours a solution of ammonia in water (0.4 ml of 25% solution) was added to the reaction mixture and the mixture was stirred for 16 h. The solvent was then evaporated and acetone (15 ml) was added to the resulting thick syrup. The resulting white precipitate was isolated by filtration on sintered glass and then suspended in a mixture of methanol (1.1 ml) and ammonia (1.1 ml). The mixture was heated in a pressure tube at 60° C. for 6 hrs, and then evaporated under reduced pressure. The residue was dissolved in a 0.01% aqueous solution of trifluoroacetic acid and purified by ultrafiltration on a membrane with 1 kDa pores (Ultracell; manufacturer Merck Millipore), and lyophilized. The yield of the mixture of isomeric compounds 3 and 9 was 41 mg (55%).

Crude mixture of isomeric compounds 3 and 9 (41 mg; 0.021 mmol) was dissolved in dry methanol (1 mL) and ethyl trifluoroacetate (0.12 mL) was added. DIPEA (0.75 mL) was then added to stirring reaction mixture in small portions within 20 minutes so as to prevent formation of insoluble suspension. The reaction was allowed to stir overnight and then it was evaporated to dryness on a rotatory evaporator. Then the crude product was purified by reversed phase HPLC on a Phenomenex Gemini column 5 µm NX-C18 250×21.2 mm (manufacturer Phenomenex®); isocratic elution ACN-water 48:52 (column loading: 20 mg of material per run), flow 14 mL/min. Elution time: minor isomer (O-3) 11: 11.1 min; major isomer (O-2) 10: 13.0 min. Yield of 10: 16 mg (41%).

Characterization: HRMS (MALDI): m/z calculated for $C_{59}H_{74}F_{21}N_7O_{35}$ [M+Na]$^+$: 1862.3788; found 1862.3791; elemental analysis (%), calculated for $C_{59}H_{74}F_{21}N_7O_{35}$: C, 38.51; H, 4.05; N, 5.33; found: C, 38.22; H, 4.15; N, 5.07. $^1$H and $^{13}$C NMR data—see FIGS. 10 and 11.

Example 13

Synthesis of conjugate 6c (FIG. 3) by alternative method using 2$^I$-O-allyl-heptakis(6-trifluoroacetamido-6-deoxy)-β-cyclodextrin 10

Compound 10 (7.5 mg; 4.08 µmol) and thiol SH—(CH$_2$)$_5$—CO-(Arg-Aca)$_8$-NH$_2$ (10 mg; 3.11 µmol) were dissolved in methanol (40 µL) containing dissolved 2,2-dimethoxy-2-phenylacetophenon (0.080 mg) under argon. The solution was irradiated with UV light of wavelength 365 nm generated by the LED (1 W) under constant stirring for 15 min. Then the reaction mixture was applied to reversed phase HPLC column (Phenomenex Gemini column 5 µm NX-C18 250×21.2 mm, manufacturer Phenomenex®) and eluted with a linear gradient A to B: from 22% B to 30% B over 15 min; 14 ml/min; where A was a 0.02% solution of TFA in water, B was 100% ACN. Retention time of intermediate product (compound 12, X=CF$_3$CONH—; Y=(-Arg-Aca)$_8$-NH—(CH$_2$)$_2$—NH$_2$)=11.8 min, yield 8.4 mg.

This intermediate product was subsequently treated with solution of aqueous ammonia diluted with water (1:3, v/v) for 4 hours and lyophilized. The lyophilizate was purified by dialysis against water (Float-a-Lyzer G2, 0.5-1 kDa MW cutoff) and lyophilized again to obtain pure conjugate 6c (6.8 mg). Analytical data are identical with that of compound 6c prepared from compound 4.

Example 14

Synthesis of 2$^I$-O-allyl-octakis(6-azido-6-deoxy)-γ-cyclodextrin 14

Octakis(6-azido-6-deoxy)-γ-cyclodextrin (165 mg, 0.11 mmol) was dissolved in dry DMF (3.4 ml) and potassium tert-butoxide solution in THF was added (1.0 mol l$^{-1}$, 0.12 ml, 0.120 mmol). The mixture was heated briefly to 40° C. The suspension was cooled to −15° C. and allyl iodide was added (0.01 ml, 0.109 mmol). The reaction mixture was stirred at −15° C. for 50 hours; during the reaction the precipitate dissolved completely. Resulted solution was poured into TBME (100 ml). The precipitate was filtered on a sintered glass, washed with TBME (3×10 ml) and dried under vacuum at room temperature. Crude product (157 mg) was dissolved in THF (2 ml) and resulted solution was coated on silica gel (1.3 g) and purified by flash chromatography (30 g silica gel, AcOEt:TBME:acetone:EtOH:water:THF; 36:40:7.2:9.6:7.2:1.6) Compound 14 was isolated in a yield of 26 mg (15%).

Characterization: HRMS (MALDI): m/z calculated for $C_{51}H_{76}N_{24}O_{32}$ [M+Na]$^+$: 1559.4955; found 1559.4961; elemental analysis (%: calculated for $C_{51}H_{76}N_{24}O_{32}$: C, 39.85; H, 4.98; N, 21.87; O, 33.30; found C: 41.37; H, 5.41; N, 19.12. $^1$H and $^{13}$C NMR data—see FIGS. 10 and 11.

Example 15

Synthesis of 2$^I$-O-allyl-octakis(6-amino-6-deoxy)-γ-cyclodextrin octakis(trifluoroacetate) 16

Compound 16 was prepared by the method described above for the preparation of compound 4.

Characterization: HRMS (MALDI): m/z calculated for $C_{51}H_{92}N_8O_{32}$ [M+H]$^+$: 1329.5890; found 1329.5873; elemental analysis (%: calculated for $C_{51}H_{92}N_8O_{32}$:C, 46.08; H, 6.98; N, 8.43; O, 38.; found C: 45.42; H, 7.93; N, 7.85.

Example 16

Figure 8:
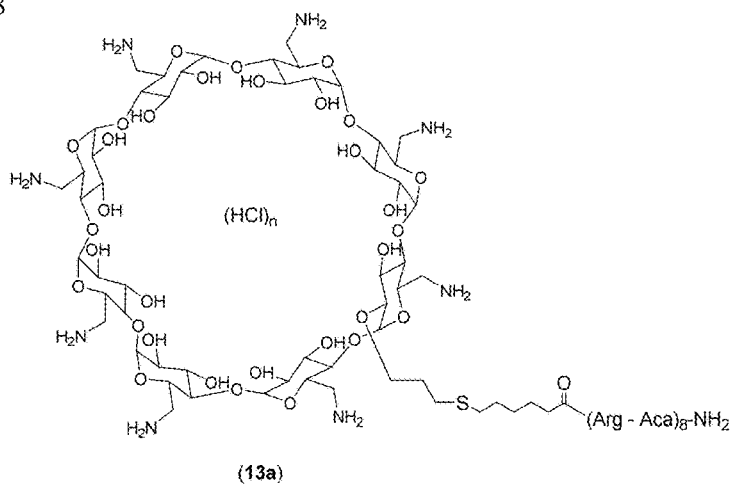
FIG. 8: Structural formula of conjugate 13a
FIG. 9: Dot chart representation of flow cytometry analysis described in Example 18.

Synthesis of Conjugate 13a (FIG. 8)

Compound 13a was prepared from compound 16 by the method described above for the preparation of compound 6c. The trifluoroacetate counterions were exchanged for Cl$^-$ by passing the aqueous solution of the material through column of Dowex-1 in Cl$^-$ cycle (0.5 mL of Dowex per 3 mg of material).

Characterization: HRMS (MALDI): for $C_{153}H_{289}N_{49}O_{49}S$ [M+H]$^+$ calculated 3629.1349; found 3629.1362; analytical HPLC: column ZORBAX Poroshell 120 SB-C18; 3×50 mm (manufacturer Agilent); 2.7 µm; linear gradient A and B: from 5% B to 20% B over 5 min; 1 ml/min; where A was a 0.02% solution of TFA in water, B was 100% ACN. Retention time of compound 13a is 3.4 min.

Example 17

Figure 9:
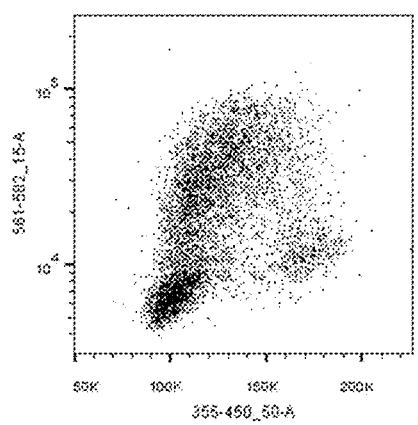

Detection of S-phase Cell Cycle Progression With DIRECT Labelling of DNA Using Compound 6c/aminoallyl-dUTP-Cy3 Complex (FIG. 9)

U2-OS cells were washed twice with the treating buffer and then treating solution of the complex (10 µM compound 6c, 10 µM aminoallyl-dUTP-Cy3 in the buffer) was added. After 3 min the solution was removed, cells were washed once with the buffer and then they were incubated in complete medium (37° C., 5% CO$_2$) for 15 min. Cells were trypsinized, washed with PBS, fixed with ethanol, washed with PBS and then treated with DAPI solution (10 µg/mL in 0.1% Triton X 100 in PBS) for 30 min at room temperature. Cells were analyzed by flow cytometry without washing (FIG. 9). Proportions of cells in phases of cell cycle were as follows: G0/G1: 30%, S: 55%, G2/M: 9%, which is in accord to proportions obtained by standard BrdU assay (G0/G1: 28%, S: 55%, G2/M: 11%).

INDUSTRIAL APPLICABILITY

Compounds of the general formulae 6 and 13 can be used in pharmaceutical research when testing the activity of novel virostatic agents based on nucleoside triphosphates. Further, they can be used in molecular and cell biology for the incorporation of labelled NTPs into DNA or RNA.

REFERENCES

1. Jordheim, L. P., Durantel, D., Zoulim, F. & Dumontet, C. (2013). Advances in the development of nucleoside and nucleotide analogues for cancer and viral diseases. *Nature Reviews Drug Discovery* 12, 447-464.
2. Hillaireau, H. & Couvreur, P. (2009). Nanoencapsulation of antiviral nucleotide analogs. *Journal of Drug Delivery Science and Technology* 19, 385-390.
3. Vinogradov, S. V., Kohli, E. & Zeman, A. D. (2005a). Cross-linked polymeric nanogel formulations of 5'-triphosphates of nucleoside analogues: Role of the cellular membrane in drug release. *Molecular Pharmaceutics* 2, 449-461.
4. Vinogradov, S. V., Zeman, A. D., Batrakova, E. V. & Kabanov, A. V. (2005b). Polyplex Nanogel formulations for drug delivery of cytotoxic nucleoside analogs. *Journal of Controlled Release* 107, 143-157.
5. Gollnest, T., de Oliveira, T. D., Schols, D., Balzarini, J. & Meier, C. (2015). Lipophilic prodrugs of nucleoside triphosphates as biochemical probes and potential antivirals. *Nature Communications* 6.
6. Mulato, A. S. & Cherrington, J. M. (1997). Anti-HIV activity of adefovir (PMEA) and PMPA in combination with antiretroviral compounds: in vitro analyses. *Antiviral Research* 36, 91-97.

The invention claimed is:

1. Compounds of general formula 6

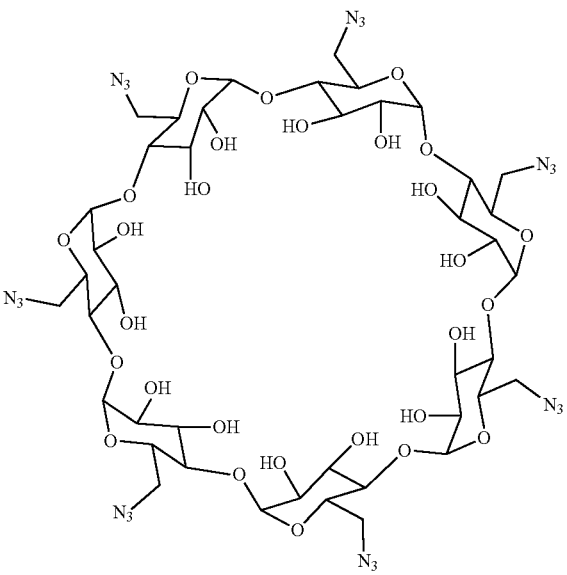
(1)

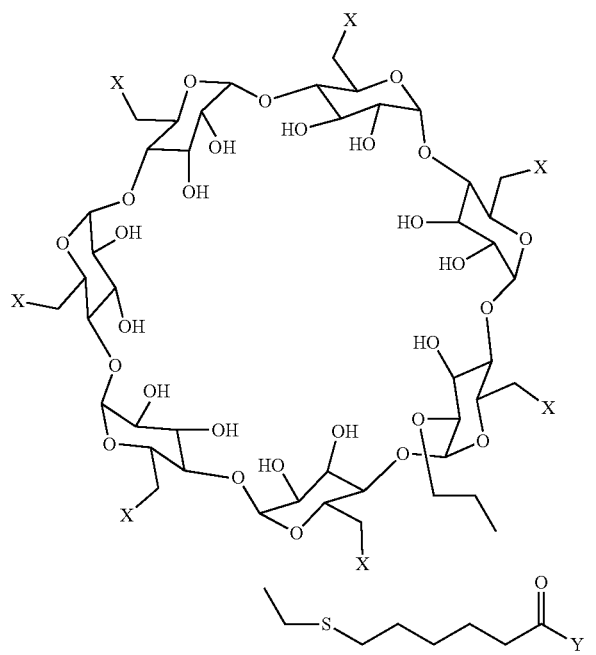
(6)

where X is —NH—C(NH$_2$)=N$^+$H$_2$ or —N$^+$H$_3$ and Y is a linear oligomer consisting of arginine units terminated with an aminodimethylenamide unit (-Arg)$_n$-NH—(CH$_2$)$_2$—NH$_2$, where n=6-10, or arginine-aminocaproic units (-Arg-Aca)$_n$-NH$_2$, where n=6 to 10, in a form of salt with pharmaceutically acceptable anion.

2. A method for the preparation of compounds of general formula 6 where X is —NH—C(NH$_2$)=N$^+$H$_2$ CF$_3$COO$^-$ and Y is a linear oligomer consisting of arginine units terminated with an aminodimethylenamide unit (-Arg)$_n$-NH—(CH$_2$)$_2$—NH$_2$, where n=6-10, or arginine-aminocaproic units (-Arg-Aca)$_n$-NH$_2$, where n=6 to 10, characterized in that the starting compound of formula 1 is converted with allyl bromide and sodium hydride in DMF to a mixture of 2$^I$-O-allyl-heptakis(6-azido-6-deoxy)-β-cyclodextrin and 3$^I$-O-allyl-heptakis(6-azido-6-deoxy)-β-cyclodextrin; this mixture is then treated with acetic anhydride, N,N-diisopropylethylamine and N,N-dimethylaminopyridine in acetonitrile at room temperature to isolate compound of structural formula 2

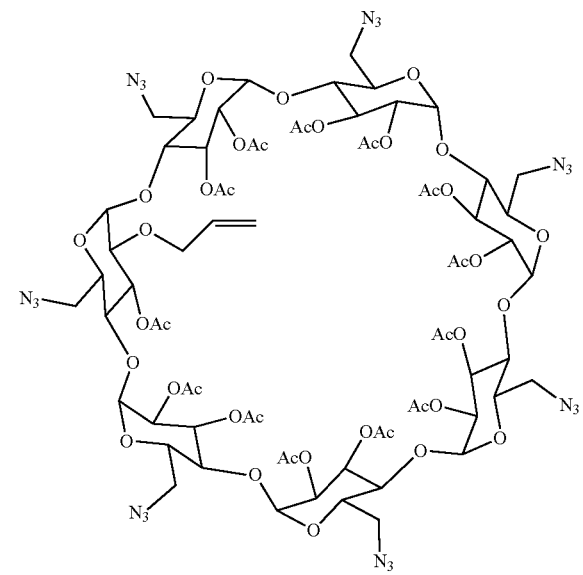
(2)

which is deacetylated in a further step, by treatment with sodium methoxide in anhydrous methanol to give the product 2$^I$-O-allyl-heptakis(6-azido-6-deoxy)-β-cyclodextrin of formula 3

(3)

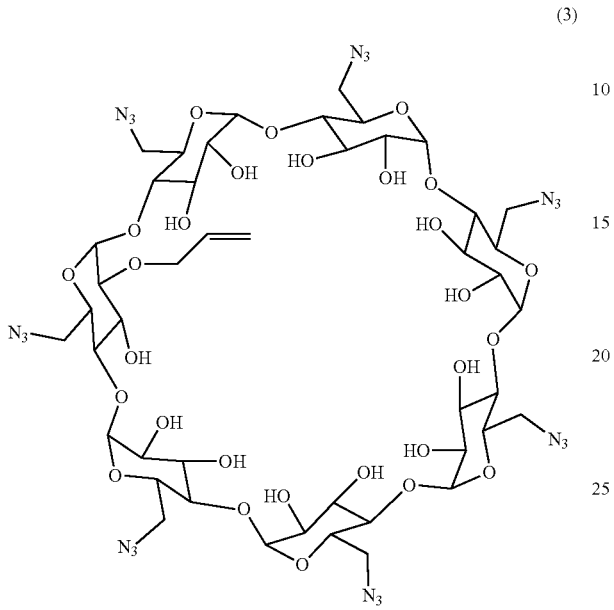

from which 2$^I$-O-allyl-heptakis(6-amino-6-deoxy)-β-cyclodextrin heptakis(trifluoro-acetate) of structural formula 4

(4)

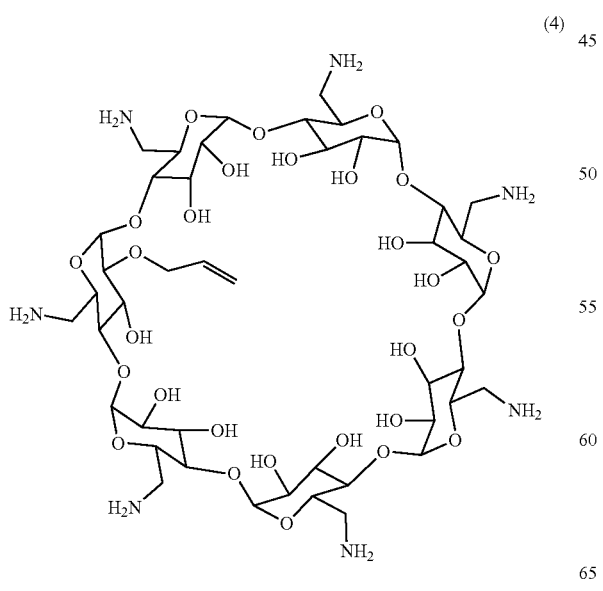

is prepared by treatment with triphenyl phosphine and aqueous ammonia in dimethylformamide, which is converted to 2$^I$-O-allyl-heptakis(6-guanidino-6-deoxy)-β-cyclodextrin heptakis(trifluoroacetate) of formula 5

(5)

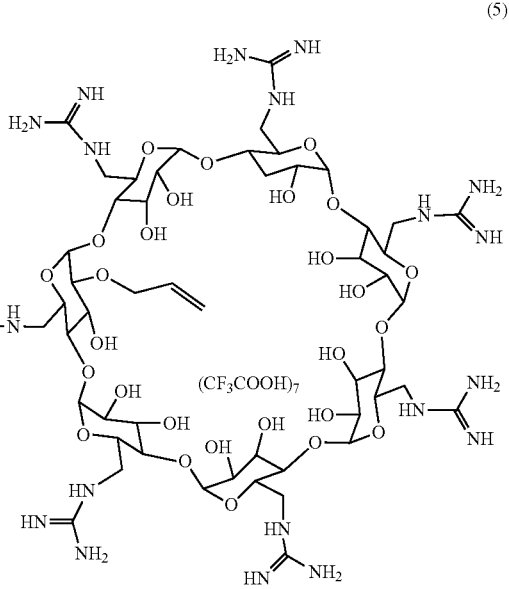

by treatment with 1H-pyrazole-1-carboxamidine hydrochloride,
and then the compound 5 is treated with the photoinitiator 2,2-dimethoxy-2-phenylacetophenone and light of wavelength 365 nm, or alternatively with a radical initiator azobisisobutyronitrile and heating, and thiols of general formulae SH—(CH$_2$)$_5$—CO-(Arg)$_n$-NH—(CH$_2$)$_2$—NH$_2$ or SH—(CH$_2$)$_5$—CO-(Arg-Aca)$_n$-NH$_2$ and converted into compounds of the general formula 6,

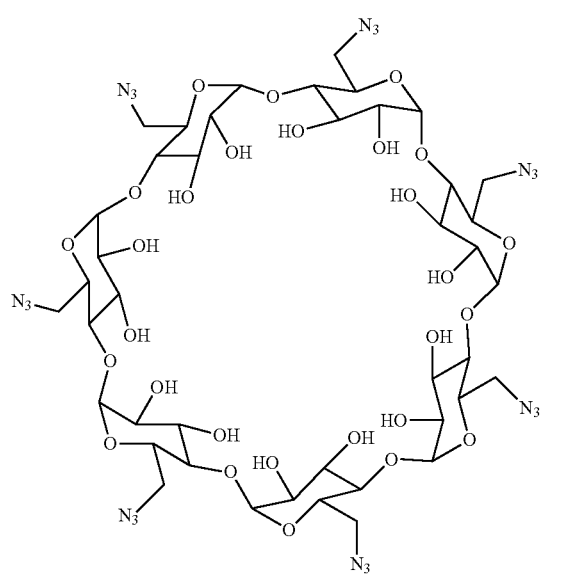

(6)

where X is —NH—C(NH$_2$)=N$^+$H$_2$ CF$_3$COO$^-$ and Y is a linear oligomer consisting of arginine units terminated with an aminodimethylenamide unit (-Arg)$_n$-NH—(CH$_2$)$_2$—NH$_2$, where n=6-10, or arginine-aminocaproic units (-Arg-Aca)$_n$-NH$_2$, where n=6 to 10.

3. Method of transporting nucleoside triphosphates across cell membranes, comprising the step of bringing into contact the compound of general formula 6 according to claim 1 and a nucleoside triphosphate and applying the resulting complex to a cell culture.

4. Method of incorporation of nucleoside triphosphates into the cellular nucleic acids, comprising the step of bringing into contact the compound of general formula 6 according to claim 1 and a nucleoside triphosphate and applying the resulting complex to a cell culture.

5. Method of determining virostatic or anticancer activity of nucleoside triphosphates, comprising the step of bringing into contact the compound of general formula 6 according to claim 1 and a nucleoside triphosphate and applying the resulting complex to a cell culture.

6. Method of determining cell proliferation and S phase of the cell cycle, comprising the step of bringing into contact the compound of general formula 6 according to claim 1 and a modified nucleoside triphosphate and applying the resulting complex to a cell culture.

7. A method for the preparation of compounds of general formula 6 according to claim 1, where X is —N$^+$H$_3$ CF$_3$COO$^-$ and Y is a linear oligomer consisting of arginine units terminated with an aminodimethylenamide unit (-Arg)$_n$-NH—(CH$_2$)$_2$—NH$_2$, where n=6-10, or arginine-aminocaproic units (-Arg-Aca)$_n$-NH$_2$, where n=6 to 10 characterized in that the starting compound of formula 1

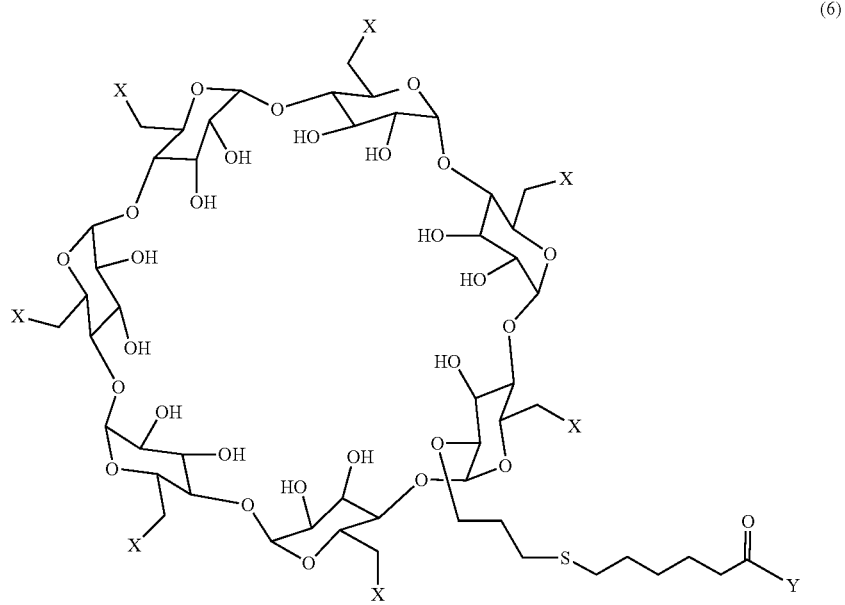

(1)

is treated with allyl bromide or allyl iodide and sodium hydride or potassium tert-butoxide in dimethylformamide to produce a mixture of 2'-(9-allyl-heptakis(6-azido-6-deoxy)-β-cyclodextrin 3 and 3'-O-allyl-heptakis(6-azido-6-deoxy)-β-cyclodextrin 9 in ratio approximately 9:1,

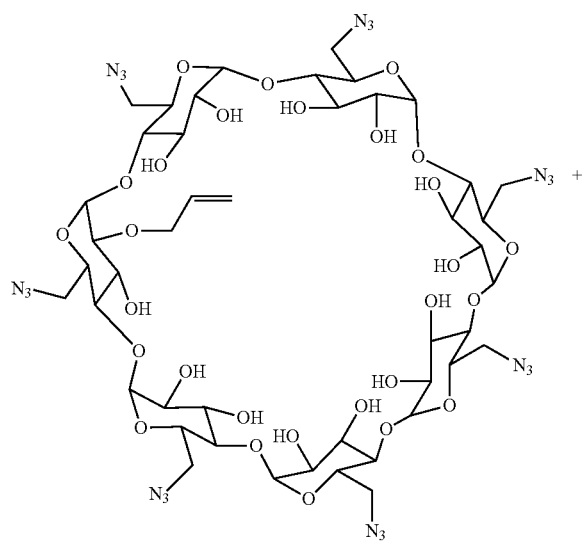

(3)

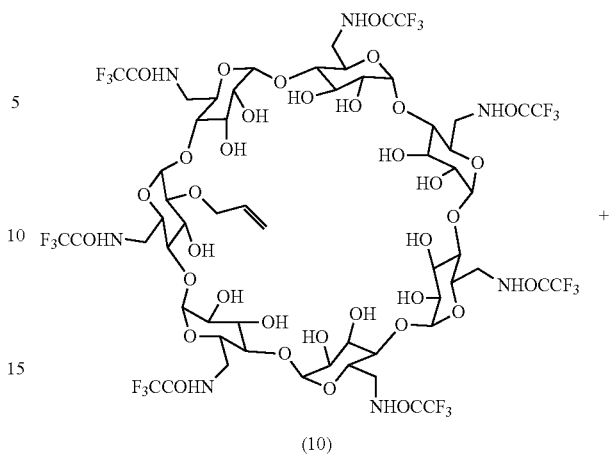

(10)

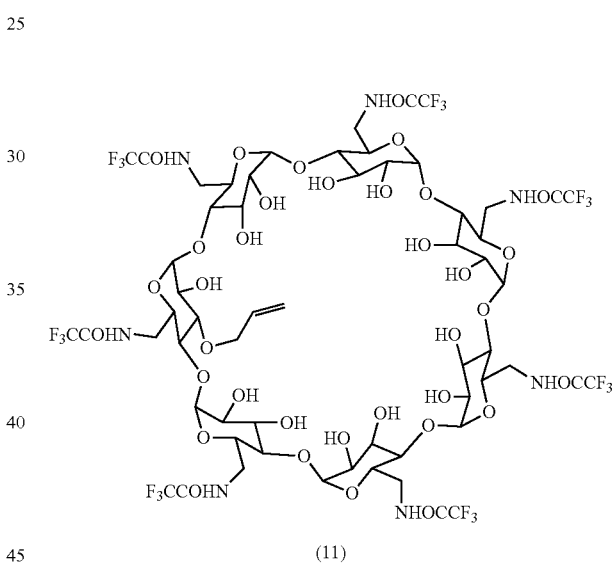

(11)

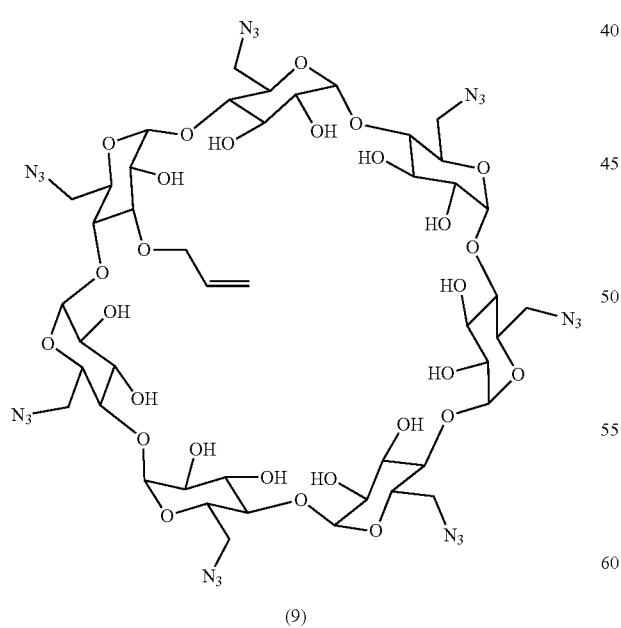

(9)

which is then treated with ethyl trifluoroacetate and DIPEA in methanol to produce a mixture of isomeric compounds 10 and 11 which are separated by means of reversed-phase HPLC; compound 10 is then treated with light of wavelength 365 nm, a photoinitiator 2,2-dimethoxy-2-phenylacetophenone (or azobisisobutyronitrile and heating) and thiols of general formulae SH—$(CH_2)_5$—CO-$(Arg)_n$-NH—$(CH_2)_2$—$NH_2$ or SH—$(CH_2)_5$—CO-$(Arg\text{-}Aca)_n$-$NH_2$, where n=6-10, and, in this way, converted to compounds of general formula 12,

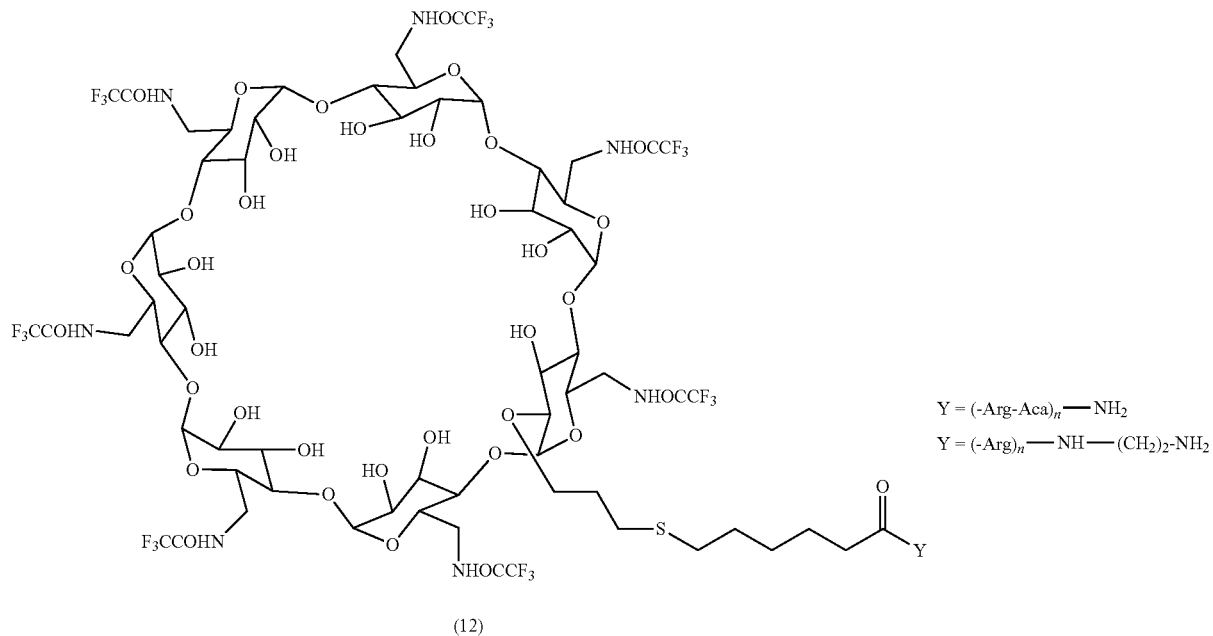

(12)

where Y is a linear oligomer consisting of arginine units terminated with an aminodimethylenamide unit $(\text{-Arg})_n\text{-NH}\text{—}(\text{CH}_2)_2\text{—}\text{NH}_2$, where n=6-10, or arginine-aminocaproic units $(\text{-Arg-Aca})_n\text{-NH}_2$, where n=6 to 10, which are subsequently treated with aqueous ammonia to remove protective groups to obtain final products of general formula 6,

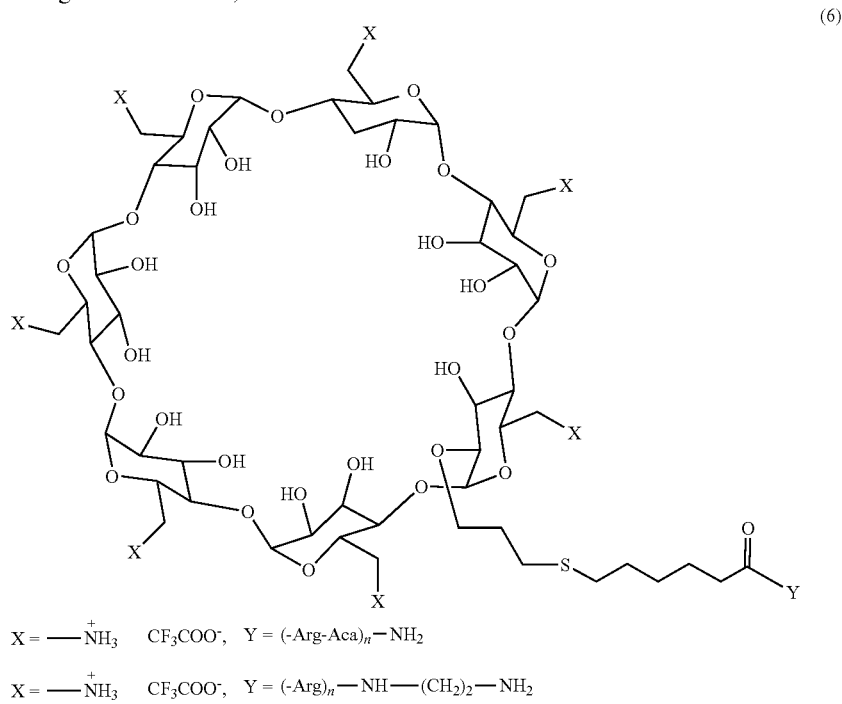

(6)

where X is $-\text{N}^+\text{H}_3\ \text{CF}_3\text{COO}^-$ and Y is a linear oligomer consisting of arginine units terminated with an aminodimethylenamide unit $(\text{-Arg})_n\text{-NH}\text{—}(\text{CH}_2)_2\text{—}\text{NH}_2$, where n=6-10, or arginine-aminocaproic units $(\text{-Arg-Aca})_n\text{-NH}_2$, where n=6 to 10.

8. Compounds of general formula 13

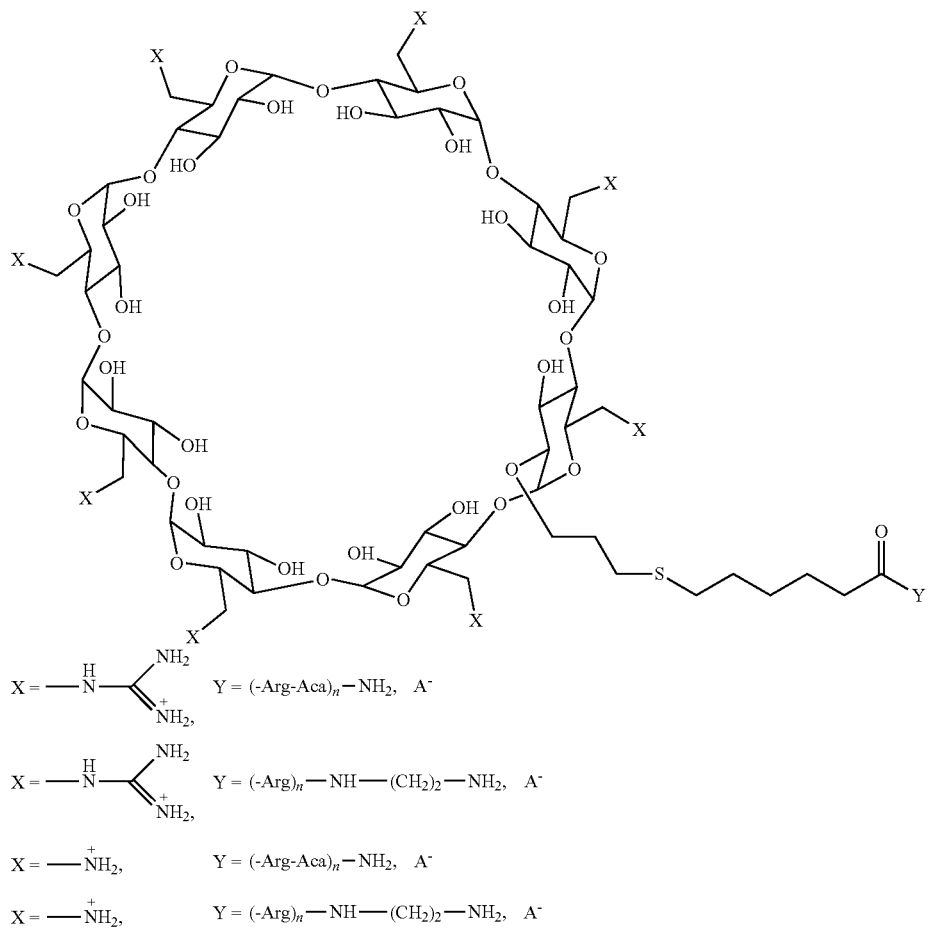

(13)

X = —N(H)—C(NH$_2$)=N$^+$H$_2$,    Y = (-Arg-Aca)$_n$—NH$_2$, A$^-$

X = —N(H)—C(NH$_2$)=N$^+$H$_2$,    Y = (-Arg)$_n$—NH—(CH$_2$)$_2$—NH$_2$, A$^-$

X = —N$^+$H$_2$,    Y = (-Arg-Aca)$_n$—NH$_2$, A$^-$

X = —N$^+$H$_2$,    Y = (-Arg)$_n$—NH—(CH$_2$)$_2$—NH$_2$, A$^-$ where X is —NH—C(NH$_2$)=N$^+$H$_2$ or —N$^+$H$_3$ and Y is a linear oligomer consisting of arginine units terminated with an aminodimethylenamide unit (-Arg)$_n$-NH—(CH$_2$)$_2$—NH$_2$, where n=6-10, or arginine-aminocaproic units (-Arg-Aca)$_n$-NH$_2$, where n=6 to 10, A$^-$ is a pharmaceutically acceptable anion; the number of counteranions is from 10 to 16 per molecule.

9. A method for the preparation of compounds of general formula 13, where X is —NH—C(NH2)=N$^+$H$_2$ and Y is a linear oligomer consisting of arginine units terminated with an aminodimethylenamide unit (-Arg)n-NH—(CH2)2-NH2, where n=6-10, or arginine-aminocaproic units (-Arg-Aca)n-NH2, where n=6 to 10, characterized in that the starting compound octakis(6-azido-6-deoxy)-γ-cyclodextrin is converted by treatment with allyl bromide or allyl iodide and sodium hydride or potassium tert-butoxide in dimethylformamide to 2$^I$-O-allyl-octakis(6-azido-6-deoxy)-γ-cyclodextrin 14

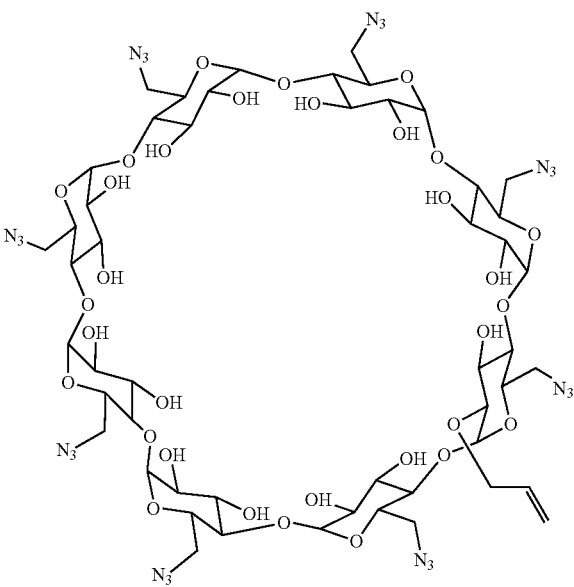

(14)

reduction of which by action of triphenylphosphine and aqueous ammonia yields 2$^I$-O-allyl-octakis(6-amino-6-deoxy)-γ-cyclodextrin 16, (16)

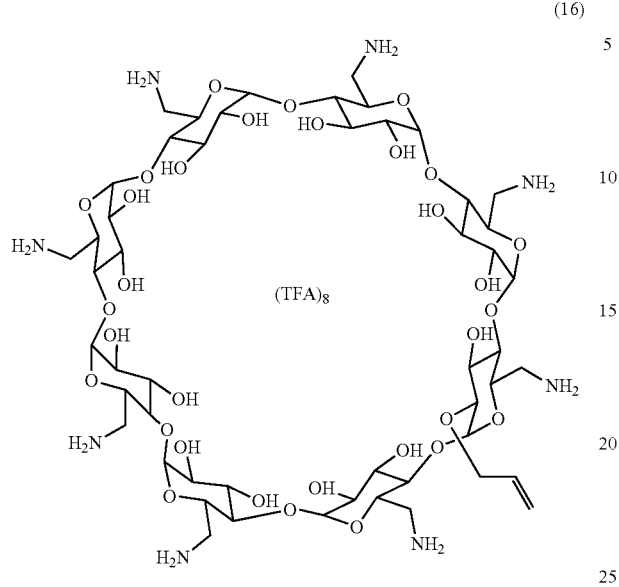

which is treated with 1H-pyrazole-1-carboxamidine hydrochloride and converted to 2$^I$-O-allyl-octakis(6-guanidino-6-deoxy)-γ-cyclodextrin octakis (trifluoroacetate) of structural formula 17;

(17)

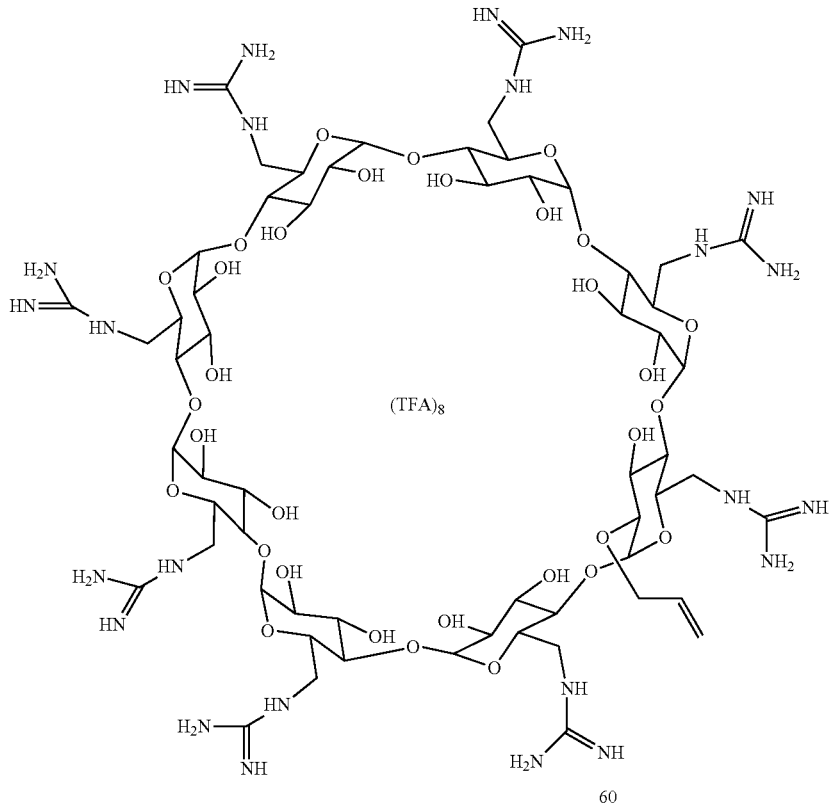

compound 17 is treated with light of wavelength 365 nm, a photoinitiator 2,2-dimethoxy-2-phenylacetophenone, or alternatively by azobisisobutyronitrile and heating, and thiols of general formulae SH—(CH$_2$)$_5$—CO-(Arg)$_n$-NH—(CH$_2$)$_2$—NH$_2$ or SH—(CH$_2$)$_5$—CO-(Arg-Aca)$_n$-NH$_2$ and, in this way, converted to compounds of general formula 13,

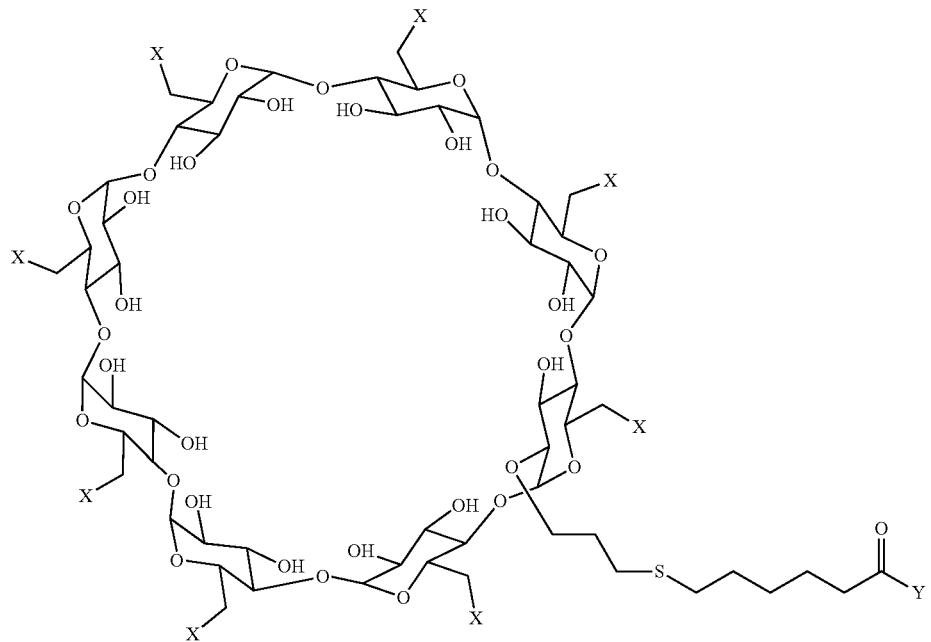

(13)

where X is —NH—C(NH$_2$)=N$^+$H$_2$ and Y is a linear oligomer consisting of arginine units terminated with an aminodimethylenamide unit (-Arg)$_n$-NH—(CH$_2$)$_2$—NH$_2$, where n=6-10, or arginine-aminocaproic units (-Arg-Aca)$_n$-NH$_2$, where n=6 to 10, A$^-$ is CF$_3$COO$^-$ or Cl$^-$; the number of counteranions varies from 10 to 16 per molecule.

10. Method of transporting nucleoside triphosphates across cell membranes, comprising the step of bringing into contact the compound of general formula 13 according to claim 8 and a nucleoside triphosphate and applying the resulting complex to a cell culture.

11. Method of incorporation of nucleoside triphosphates into the cellular nucleic acids, comprising the step of bringing into contact the compound of general formula 13 according to claim 8 and a nucleoside triphosphate and applying the resulting complex to a cell culture.

12. Method of determining virostatic or anti cancer activity of nucleoside triphosphates, comprising the step of bringing into contact the compound of general formula 13 according to claim 8 and a nucleoside triphosphate and applying the resulting complex to a cell culture.

13. Method of determining cell proliferation and S phase of the cell cycle, comprising the step of bringing into contact the compound of general formula 13 according to claim 8 and a modified nucleoside triphosphate and applying the resulting complex to a cell culture.

14. Compounds of general formula 6

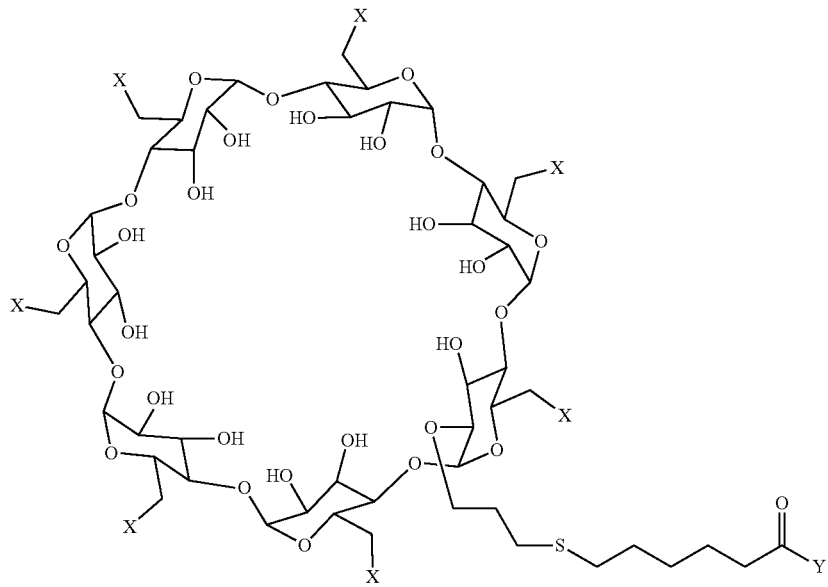

(6)

where X is —NH—C(NH$_2$)=N$^+$H$_2$ or —N$^+$H$_3$ and Y is a linear oligomer consisting of arginine units terminated with an aminodimethylenamide unit (-Arg)n-NH—(CH$_2$)$_2$—NH$_2$, where n=6-10, or arginine-aminocaproic units (-Arg-Aca)n-NH$_2$, where n=6 to 10, in a form of salt with pharmaceutically acceptable anion, or
compounds of general formula 13

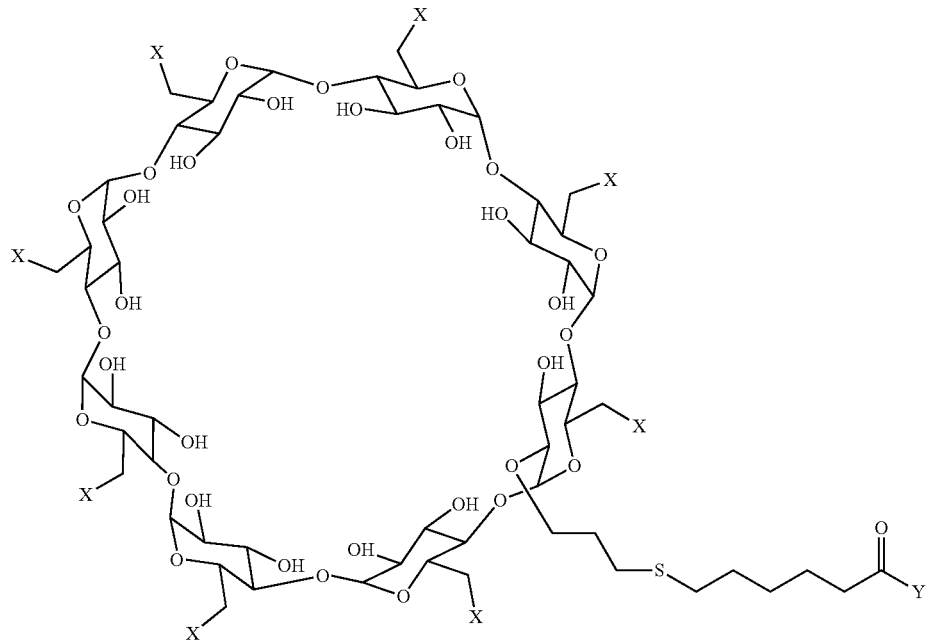

(13)

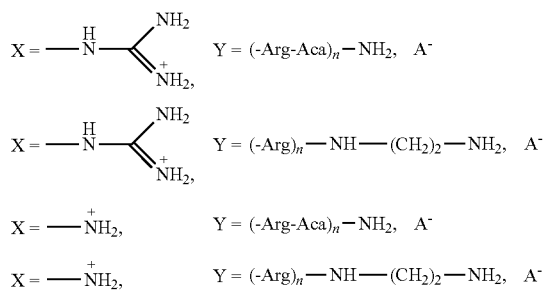

where X is —NH—C(NH$_2$)=N$^+$H$_2$ or —N$^+$H$_3$ and Y is a linear oligomer consisting of arginine units terminated with an aminodimethylenamide unit (-Arg)$_n$-NH—(CH$_2$)$_2$—NH$_2$, where n=6-10, or arginine-aminocaproic units (-Arg-Aca)$_n$-NH$_2$, where n=6 to 10, A$^-$ is a pharmaceutically acceptable anion; the number of counteranions is from 10 to 16 per molecule, where some or all arginine units in said general formula 6 or 13 are replaced with naturally occurred amino acids containing guanidine moiety or guanidino peptidomimetics chosen from norarginine, homoarginine and β-homoarginine.

15. Compounds of general formula 6
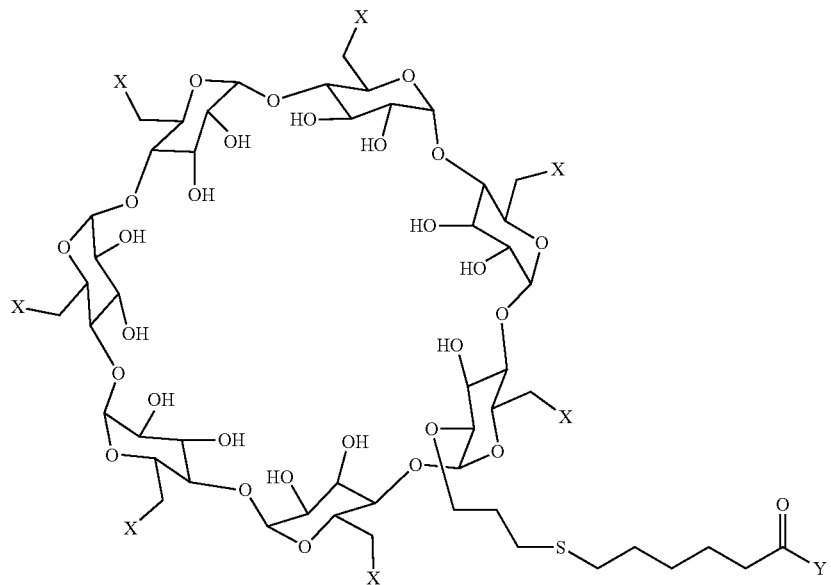
(6)
where X is —NH—C(NH$_2$)=N$^+$H$_2$ or —N$^+$H$_3$ and Y is a linear oligomer consisting of arginine units terminated with an aminodimethylenamide unit (-Arg)$_n$-NH—(CH$_2$)$_2$—NH$_2$, where n=6-10, or arginine-aminocaproic units (-Arg-Aca)$_n$-NH$_2$, where n=6 to 10, in a form of salt with pharmaceutically acceptable anion, or
compounds of general formula 13
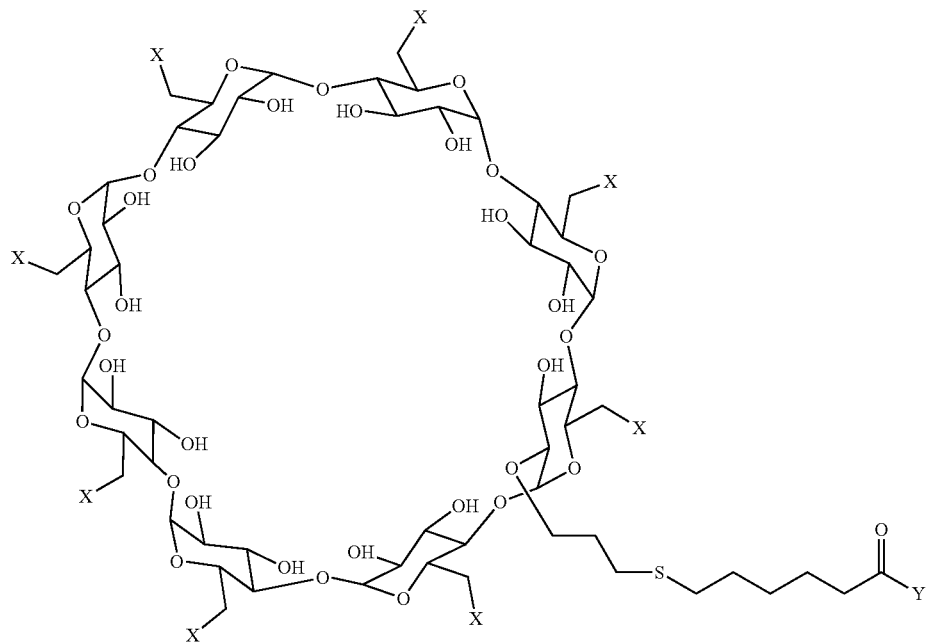
(13)

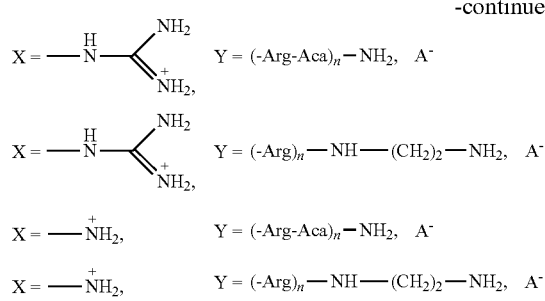

where X is —NH—C(NH$_2$)=N$^+$H$_2$ or —N$^+$H$_3$ and Y is a linear oligomer consisting of arginine units units terminated with an aminodimethylenamide unit (-Arg)n-NH—(CH2)2-NH2, where n=6-10, or arginine-aminocaproic units (-Arg-Aca)$_n$-NH2, where n=6 to 10, A- is a pharmaceutically acceptable anion; the number of counteranions is from 10 to 16 per molecule, where some or all amido groups are replaced by different functional groups chosen from ester group, amine group, carbamate group or ether group.

16. Compounds of general formula 6 according to claim 1, wherein the pharmaceutically acceptable anion is CF$_3$COO$^-$ or a chloride form.

17. Compounds of general formula 13 according to claim 8, wherein the pharmaceutically acceptable anion is CF$_3$COO— or Cl$^-$.

18. A method for the preparation of compounds of general formula 6 where X is —N$^+$H$_3$ CF$_3$COO$^-$ and Y is a linear oligomer consisting of arginine units terminated with an aminodimethylenamide unit (-Arg)$_n$-NH—(CH$_2$)$_2$—NH$_2$, where n=6-10, or arginine-aminocaproic units (-Arg-Aca)$_n$-NH$_2$, where n=6 to 10, characterized in that the starting compound of formula 1

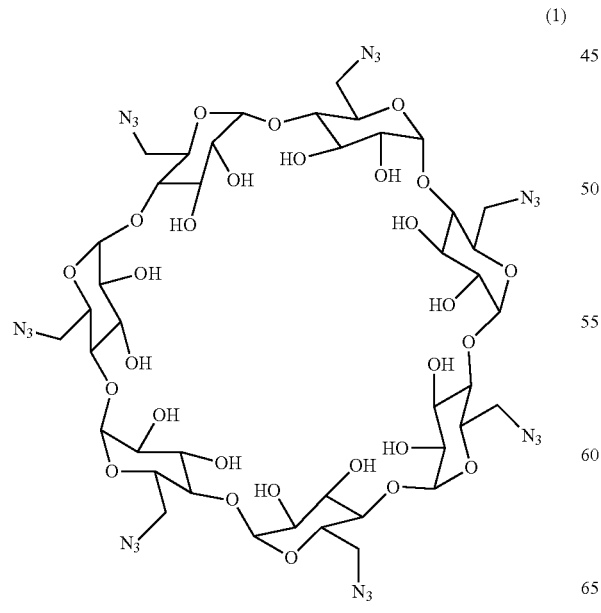

(1)

is converted with allyl bromide and sodium hydride in DMF to a mixture of 2$^I$-O-allyl-heptakis(6-azido-6-deoxy)-β-cyclodextrin and 3$^I$-O-allyl-heptakis(6-azido-6-deoxy)-β-cyclodextrin; this mixture is then treated with acetic anhydride, N,N-diisopropylethylamine and N,X-dimethylaminopyridine in acetonitrile at room temperature to isolate compound of structural formula 2,

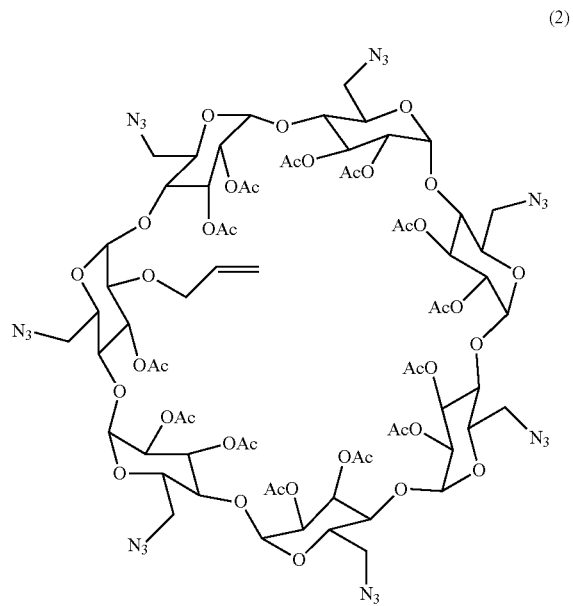 [SMILES: C=CCOC1C2OC(CN=[N+]=[N-])C(OC3OC(CN=[N+]=[N-])C(OC4OC(CN=[N+]=[N-])C(OC5OC(CN=[N+]=[N-])C(OC6OC(CN=[N+]=[N-])C(OC7OC(CN=[N+]=[N-])C(OC8OC(CN=[N+]=[N-])C(O2)C(OC(C)=O)C8OC(C)=O)C(OC(C)=O)C7OC(C)=O)C(OC(C)=O)C6OC(C)=O)C(OC(C)=O)C5OC(C)=O)C(OC(C)=O)C4OC(C)=O)C(OC(C)=O)C3OC(C)=O)C1OC(C)=O]

(2)

which is deacetylated in a further step, by treatment with sodium methoxide in anhydrous methanol to give the product 2$^I$-O-allyl-heptakis(6-azido-6-deoxy)-β-cyclodextrin of formula 3,

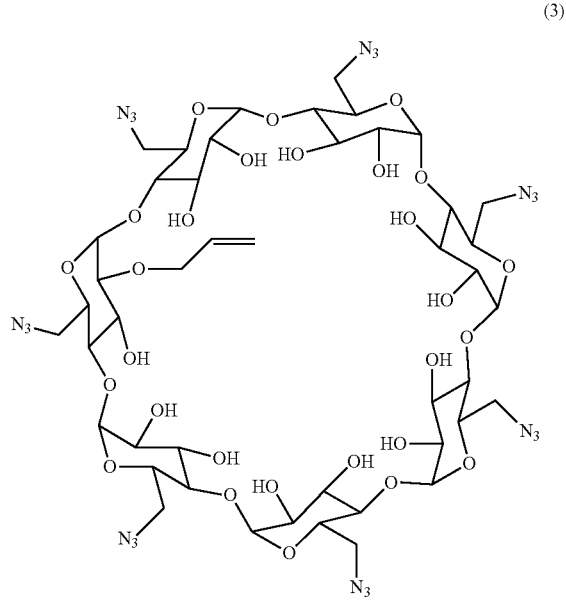 [SMILES: C=CCOC1C2OC(CN=[N+]=[N-])C(OC3OC(CN=[N+]=[N-])C(OC4OC(CN=[N+]=[N-])C(OC5OC(CN=[N+]=[N-])C(OC6OC(CN=[N+]=[N-])C(OC7OC(CN=[N+]=[N-])C(OC8OC(CN=[N+]=[N-])C(O2)C(O)C8O)C(O)C7O)C(O)C6O)C(O)C5O)C(O)C4O)C(O)C3O)C1O]

(3)

from which 2^I-O-allyl-heptakis(6-amino-6-deoxy)-β-cyclodextrin heptakis(trifluoro-acetate) of structural formula 4

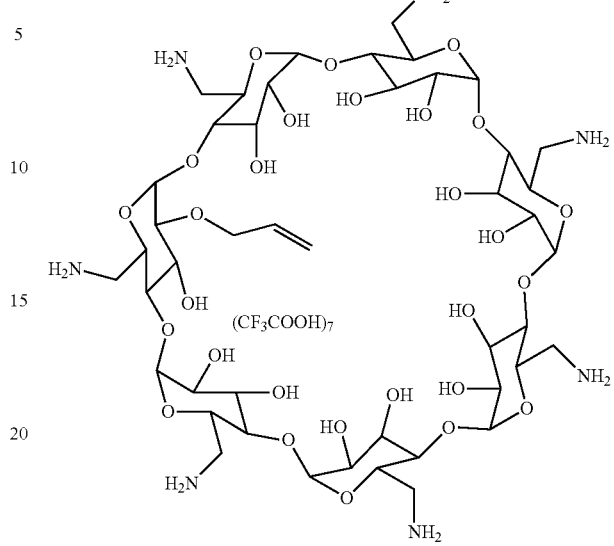

(4)

is prepared by treatment with triphenyl phosphine and aqueous ammonia in dimethylformamide, and then the compound 4 is treated with the photoinitiator 2,2-dimethoxy-2-phenylacetophenone and light of wavelength 365 nm, or alternatively with a radical initiator azobisisobutyronitrile and heating, and thiols of general formulae SH—(CH$_2$)$_5$—CO-(Arg)$_n$-NH—(CH$_2$)$_2$—NH$_2$ or SH—(CH$_2$)$_5$—CO-(Arg-Aca)$_n$-NH$_2$ to obtain compounds of the formula 6,

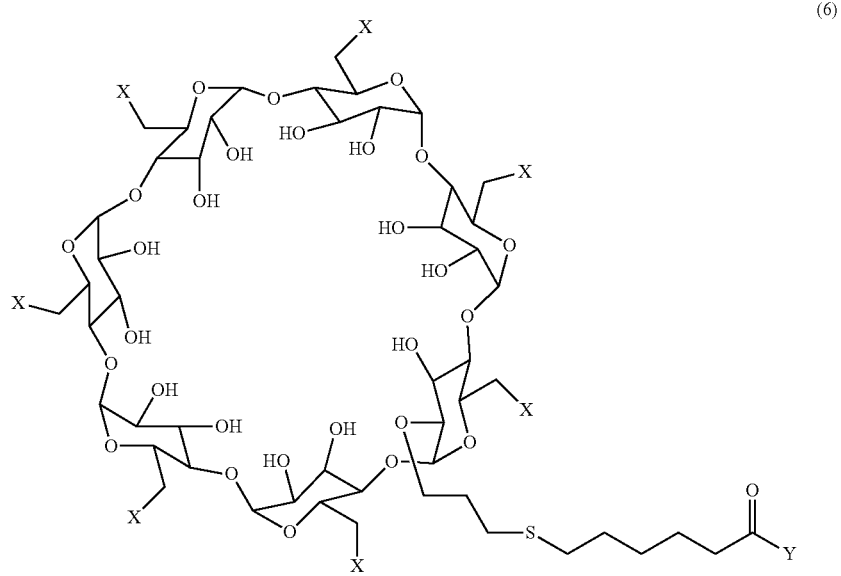

(6)

where X is —N⁺H₃ CF₃COO⁻ and Y is a linear oligomer consisting of arginine units terminated with an aminodimethylenamide unit (-Arg)$_n$-NH—(CH₂)₂—NH₂, where n=6-10, or arginine-aminocaproic units (-Arg-Aca)$_n$-NH₂, where n=6 to 10.

19. A method for the preparation of compounds of general formula 13, where X is —N⁺H₃ and Y is a linear oligomer consisting of arginine units terminated with an aminodimethylenamide unit (-Arg)$_n$-NH—(CH₂)₂—NH₂, where n=6-10, or arginine-aminocaproic units (-Arg-Aca)$_n$-NH₂, where n=6 to 10, A⁻ is CF₃COO⁻ or Cl, characterized in that the starting compound octakis(6-azido-6-deoxy)-γ-cyclodextrin is converted by treatment with allyl bromide or allyl iodide and sodium hydride or potassium tert-butoxide in dimethylformamide to 2$^I$-O-allyl-octakis(6-azido-6-deoxy)-γ-cyclodextrin 14

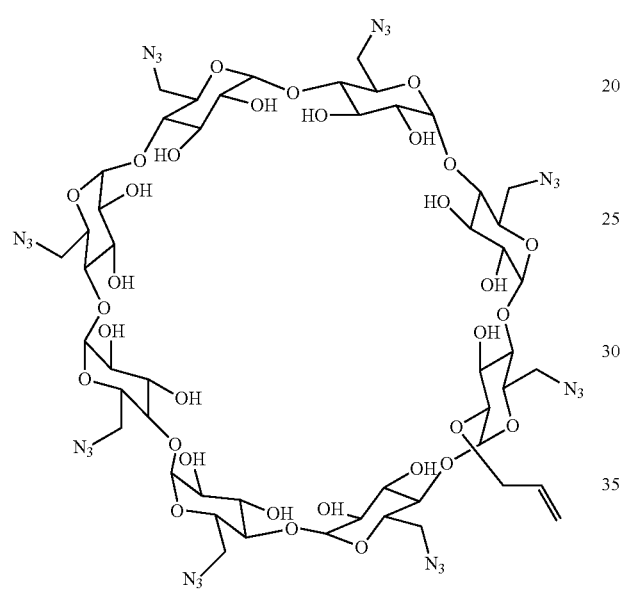

(14)

reduction of which by action of triphenylphosphine and aqueous ammonia yields 2$^I$-O-allyl-octakis(6-amino-6-deoxy)-γ-cyclodextrin 16;

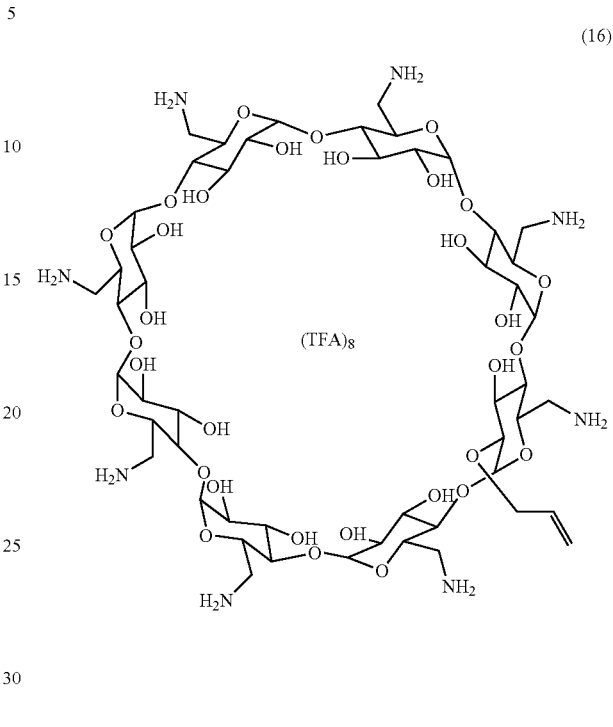

(16)

compound 16 is treated with light of wavelength 365 nm, a photoinitiator 2,2-dimethoxy-2-phenylacetophenone, or alternatively with azobisisobutyronitrile and heating, and thiols of general formulae SH—(CH₂)₅—CO-(Arg)$_n$-NH—(CH₂)₂—NH₂ or SH—(CH₂)₅—CO-(Arg-Aca)$_n$-NH₂ and, in this way, converted to compounds of general formula 13,

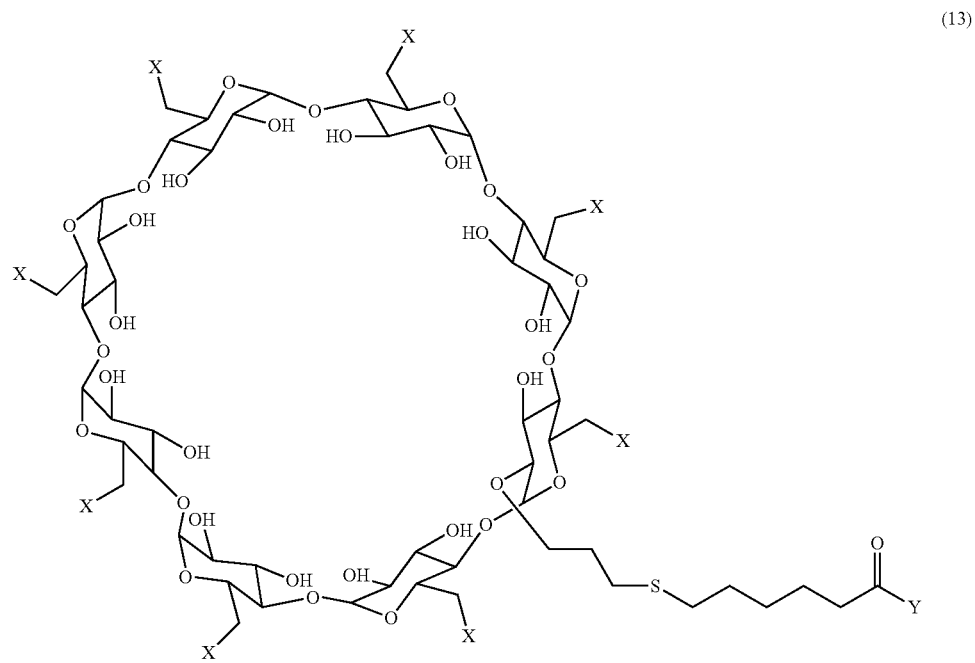

(13)

where X is $-N^+H_3$ and Y is a linear oligomer consisting of arginine units terminated with an aminodimethylenamide unit $(-Arg)_n-NH-(CH_2)_2-NH_2$, where n=6-10, or arginine-aminocaproic units $(-Arg-Aca)_n-NH_2$, where n=6 to 10, $A^-$ is $CF_3COO^-$ or $Cl^-$; the number of counteranions varies from 10 to 16 per molecule.

* * * * *